US010472650B2

(12) United States Patent
Davidson et al.

(10) Patent No.: US 10,472,650 B2
(45) Date of Patent: Nov. 12, 2019

(54) METHODS AND COMPOSITIONS FOR TREATING GENETIC EYE DISEASES

(71) Applicants: UNIVERSITY OF IOWA RESEARCH FOUNDATION, Iowa City, IA (US); FONDAZIONE TELETHON, Rome (IT)

(72) Inventors: Beverly L Davidson, Iowa City, IA (US); Yong Hong Chen, Iowa City, IA (US); Alberto Auricchio, Naples (IT)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 15/551,869

(22) PCT Filed: Feb. 22, 2016

(86) PCT No.: PCT/US2016/018970
§ 371 (c)(1),
(2) Date: Dec. 19, 2017

(87) PCT Pub. No.: WO2016/134375
PCT Pub. Date: Aug. 25, 2016

(65) Prior Publication Data
US 2018/0142259 A1 May 24, 2018

Related U.S. Application Data

(60) Provisional application No. 62/118,934, filed on Feb. 20, 2015.

(51) Int. Cl.
*C12N 7/00* (2006.01)
*C12N 15/00* (2006.01)
(Continued)

(52) U.S. Cl.
CPC ...... *C12N 15/8616* (2013.01); *A61K 48/0058* (2013.01); *A61P 27/00* (2018.01);
(Continued)

(58) Field of Classification Search
None
See application file for complete search history.

(56) References Cited

U.S. PATENT DOCUMENTS 6,329,501 B1    12/2001    Smith et al.
6,399,575 B1 *   6/2002    Smith ............... C07K 7/06
                                              514/17.7
(Continued)

FOREIGN PATENT DOCUMENTS

WO    2012145601 A2    10/2012
WO    2013159036 A1    10/2013
WO    2014124282 A1     8/2014

OTHER PUBLICATIONS

Gaudana et al., "Ocular Drug Delivery", AAPS J 12(3): 348-360 (2010)) (Year: 2010).*
(Continued)

Primary Examiner — M Franco G Salvoza
(74) Attorney, Agent, or Firm — Viksnins Harris Padys Malen LLP

(57) ABSTRACT

The present disclosure provides targeting peptides and vectors containing a sequence that encodes targetting peptides that deliver agents, to the eye. The present inventors have discovered peptides that function to target agents, such as viral vectors, to ocular cells. The present disclosure describes a method to utilize these novel peptides to direct, for example, viral capsids to the cell type of interest. In this instance, ocular cells (such as retinal cells) are targeted by (Continued)

the identified peptides. Vectors harboring capsid proteins modified to include such peptides can be used to provide therapeutic agents to the eye.

21 Claims, 15 Drawing Sheets

Specification includes a Sequence Listing.

(51) Int. Cl.
| | |
|---|---|
| A61K 39/23 | (2006.01) |
| C12N 15/861 | (2006.01) |
| C12N 15/86 | (2006.01) |
| A61P 27/00 | (2006.01) |
| A61K 48/00 | (2006.01) |
| C07K 14/005 | (2006.01) |

(52) U.S. Cl.
CPC .......... *C07K 14/005* (2013.01); *C12N 15/86* (2013.01); *A61K 48/0008* (2013.01); *C12N 2750/14122* (2013.01); *C12N 2750/14145* (2013.01); *C12N 2810/50* (2013.01)

(56) References Cited

U.S. PATENT DOCUMENTS

| | | | |
|---|---|---|---|
| 6,943,153 B1* | 9/2005 | Manning, Jr. .......... | A61K 48/00 424/233.1 |
| 2002/0192823 A1 | 12/2002 | Bartlett | |
| 2007/0243526 A1 | 10/2007 | Kay et al. | |
| 2009/0215879 A1* | 8/2009 | Diprimio .......... | A61K 31/7088 514/44 R |
| 2010/0081707 A1* | 4/2010 | Ali .................. | A61F 9/0017 514/44 R |
| 2011/0052666 A1* | 3/2011 | Kaemmerer .......... | A61K 9/0004 424/450 |

OTHER PUBLICATIONS

Berns, "Parvoviridae and their replication", Virology 2 (62), 1743-1763 (1990).

Boye, et al., "The Human Rhodopsin Kinase Promoter in an AAV5 Vector Confers Rod- and Cone-Specific Expression in the Primate Retina", Human Gene Therapy 23(10), 1101-1115 (2012).

Dalkara, et al., "In vivo-directed evolution of a new adeno-associated virus for therapeutic outer retinal gene delivery from the vitreous", Science Translational Medicine 5 (189), 189ra76, 12 pages (2013).

Davidson, et al., "Recombinant adeno-associated virus type 2, 4, and 5 vectors: Transduction of variant cell types and regions in the mammalian central nervous system.", Proc Natl Acad Sci USA 97(7), 3428-3432 (2000).

Klimczak, et al., "A novel adeno-associated viral variant for efficient and selective intravitreal transduction of rat Muller cells", PLoS Once 4(10), e7467, 10 pages (2009).

Kotin, "Prospects for the use of adeno-associated virus as a vector for human gene therapy", Human Gene Therapy 5, 793-801 (1994).

Patent Cooperation Treaty, International Searching Authority, Search Report and Written Opinion for PCT/US2016/018970, 11 pages, dated Jun. 9, 2016.

Petrs-Silva, et al., "High-efficiency transduction of the mouse retina by tyrosine-mutant AAV serotype vectors", Molecular Therapy 17(3), 463-471 (2009).

Sullivan, et al., "Rationally designed AAV2 and AAVrh8R capsids provide improved transduction in the retina and brain", Gene Therapy 25, 205-219 (2018).

Work, et al., "Development of Efficient Viral Vectors Selective for Vascular Smooth Muscle Cells", Molecular Therapy 9(2), 198-208 (2004).

Zinn, et al., "In Silico Reconstruction of the Viral Evolutionary Lineage Yields a Potent Gene Therapy Vector", Cell Reports 12, 1056-1068 (2015).

* cited by examiner

Figure 1A

PMAAV-GST

AAV2/2 capsid sequence (*Italicized*)
GST retina target peptide (Bold and underlined)

AATTCCCATCATCAATAATATACCTTATTTTGGATTGAAGCCAATATGATAATGAGGGG
GTGGAGTTTGTGACGTGGCGCGGGGCGTGGGAACGGGGCGGGTGACGTAGTAGTCTCTA
GAGTCCTGTATTAGAGGTCACGTGAGTGTTTTGCGACATTTTGCGACACCATGTGGTCAC
GCTGGGTATTTAAGCCCGAGTGAGCACGCAGGGTCTCCATTTTGAAGCGGGAGGTTTGA
ACGCGCAGCCGCCATGCCGGGGTTTTACGAGATTGTGATTAAGGTCCCCAGCGACCTTGA
CGGGCATCTGCCCGGCATTTCTGACAGCTTTGTGAACTGGGTGGCCGAGAAGGAATGGGA
GTTGCCGCCAGATTCTGACATGGATCTGAATCTGATTGAGCAGGCACCCCTGACCGTGGC
CGAGAAGCTGCAGCGCGACTTTCTGACGGAATGGCGCCGTGTGAGTAAGGCCCCGGAGGC
CCTTTTCTTTGTGCAATTTGAGAAGGGAGAGAGCTACTTCCACATGCACGTGCTCGTGGA
AACCACCGGGGTGAAATCCATGGTTTTGGGACGTTTCCTGAGTCAGATTCGCGAAAAACT
GATTCAGAGAATTTACCGCGGGATCGAGCCGACTTTGCCAAACTGGTTCGCGGTCACAAA
GACCAGAAATGGCGCCGGAGGCGGGAACAAGGTGGTGGATGAGTGCTACATCCCCAATT
ACTTGCTCCCCAAAACCCAGCCTGAGCTCCAGTGGGCGTGGACTAATATGGAACAGTATT
TAAGCGCCTGTTTGAATCTCACGGAGCGTAAACGGTTGGTGGCGCAGCATCTGACGCACG
TGTCGCAGACGCAGGAGCAGAACAAAGAGAATCAGAATCCCAATTCTGATGCGCCGGTG
ATCAGATCAAAAACTTCAGCCAGGTACATGGAGCTGGTCGGGTGGCTCGTGGACAAGGG
GATTACCTCGGAGAAGCAGTGGATCCAGGAGGACCAGGCCTCATACATCTCCTTCAATGC
GGCCTCCAACTCGCGGTCCCAAATCAAGGCTGCCTTGGACAATGCGGGAAAGATTATGAG
CCTGACTAAAACCGCCCCCGACTACCTGGTGGGCCAGCAGCCCGTGGAGGACATTTCCAG
CAATCGGATTTATAAAATTTTGGAACTAAACGGGTACGATCCCCAATATGCGGCTTCCGT
CTTTCTGGGATGGGCCACGAAAAAGTTCGGCAAGAGGAACACCATCTGGCTGTTTGGGCC
TGCAACTACCGGGAAGACCAACATCGCGGAGGCCATAGCCCACACTGTGCCCTTCTACGG
GTGCGTAAACTGGACCAATGAGAACTTTCCCTTCAACGACTGTGTCGACAAGATGGTGAT
CTGGTGGGAGGAGGGGAAGATGACCGCCAAGGTCGTGGAGTCGGCCAAAGCCATTCTCG
GAGGAAGCAAGGTGCGCGTGGACCAGAAATGCAAGTCCTCGGCCCAGATAGACCCGACTC
CCGTGATCGTCACCTCCAACACCAACATGTGCGCCGTGATTGACGGGAACTCAACGACCT
TCGAACACCAGCAGCCGTTGCAAGACCGGATGTTCAAATTTGAACTCACCCGCCGTCTGG
ATCATGACTTTGGGAAGGTCACCAAGCAGGAAGTCAAAGACTTTTTCCGGTGGGCAAAG
GATCACGTGGTTGAGGTGGAGCATGAATTCTACGTCAAAAAGGGTGGAGCCAAGAAAAG
ACCCGCCCCCAGTGACGCAGATATAAGTGAGCCCAAACGGGTGCGCGAGTCAGTTGCGCA
GCCATCGACGTCAGACGCGGAAGCTTCGATCAACTACGCAGACAGGTACCAAAACAAATG
TTCTCGTCACGTGGGCATGAATCTGATGCTGTTTCCCTGCAGACAATGCGAGAGAATGAA
TCAGAATTCAAATATCTGCTTCACTCACGGACAGAAAGACTGTTTAGAGTGCTTTCCCGT
GTCAGAATCTCAACCCGTTTCTGTCGTCAAAAAGGCGTATCAGAAACTGTGCTACATTCA
TCATATCATGGGAAAGGTGCCAGACGCTTGCACTGCCTGCGATCTGGTCAATGTGGATTT
GGATGACTGCATCTTTGAACAATAAATGATTTAAATCAGGT*ATGGCTGCCGATGGTTATC*
*TTCCAGATTGGCTCGAGGACACTCTCTCTGAAGGAATAAGACAGTGGTGGAAGCTCAAACCT*
*GGCCCACCACCACCAAAGCCCGCAGAGCGGCATAAGGACGACAGCAGGGGTCTTGTGCTTCCT*
*GGGTACAAGTACCTCGGACCCTTCAACGGACTCGACAAGGGAGAGCCGGTCAACGAGGCAGA*
*CGCCGCGGCCCTCGAGCACGACAAAGCCTACGACCGGCAGCTCGACAGCGGAGACAACCCGTA*

Figure 1B

*CCTCAAGTACAACCACGCCGACGCGGAGTTTCAGGAGCGCCTTAAAGAAGATACGTCTTTTGG*
*GGGCAACCTCGGACGAGCAGTCTTCCAGGCGAAAAGAGGGTTCTTGAACCTCTGGGCCTGG*
*TTGAGGAACCTGTTAAGACGGCTCCGGGAAAAAGAGGCCGGTAGAGCACTCTCCTGTGGAG*
*CCAGACTCCTCCTCGGGAACCGGAAAGGCGGGCCAGCAGCCTGCAAGAAAAGATTGAATTT*
*TGGTCAGACTGGAGACGCAGACTCAGTACCTGACCCCCAGCCTCTCGGACAGCCACCAGCAGC*
*CCCCTCTGGTCTGGGAACTAATACGATGGCTACAGGCAGTGGCGCACCAATGGCAGACAATA*
*ACGAGGGCGCCGACGGAGTGGGTAATTCCTCGGGAAATTGGCATTGCGATTCCACATGGATG*
*GGCGACAGAGTCATCACCACCAGCACCCGAACCTGGGCCCTGCCCACCTACAACAACCACCTC*
*TACAAACAAATTTCCAGCCAATCAGGAGCCTCGAACGACAATCACTACTTTGGCTACAGCACC*
*CCTTGGGGGTATTTTGACTTCAACAGATTCCACTGCCACTTTTCACCACGTGACTGGCAAAGA*
*CTCATCAACAACAACTGGGGATTCCGACCCAAGAGACTCAACTTCAAGCTCTTTAACATTCAA*
*GTCAAAGAGGTCACGCAGAATGACGGTACGACGACGATTGCCAATAACCTTACCAGCACGGT*
*TCAGGTGTTTACTGACTCGGAGTACCAGCTCCCGTACGTCCTCGGCTCGGCGCATCAAGGATG*
*CCTCCCGCCGTTCCAGCAGACGTCTTCATGGTGCCACAGTATGGATACCTCACCCTGAACAA*
*CGGGAGTCAGGCAGTAGGACGCTCTTCATTTTACTGCCTGGAGTACTTTCCTTCTCAGATGCT*
*GCGTACCGGAAACAACTTTACCTTCAGCTACACTTTTGAGGACGTTCCTTTCCACAGCAGCTA*
*CGCTCACAGCCAGAGTCTGGACCGTCTCATGAATCCTCTCATCGACCAGTACCTGTATTACTT*
*GAGCAGAACAAACACTCCAAGTGGAACCACCACGCAGTCAAGGCTTCAGTTTTCTCAGGCCGG*
*AGCGAGTGACATTCGGGACCAGTCTAGGAACTGGCTTCCTGGACCCTGTTACCGCCAGCAGCG*
*AGTATCAAAGACATCTGCGGATAACAACAACAGTGAATACTCGTGGACTGGAGCTACCAAGT*
*ACCACCTCAATGGCAGAGACTCTCTGGTGAATCCGGGCCCGGCCATGGCAAGCCACAAGGACG*
*ATGAAGAAAAGTTTTTTCCTCAGAGCGGGGTTCTCATCTTTGGGAAGCAAGGCTCAGAGAAA*
*ACAAATGTGGACATTGAAAAGGTCATGATTACAGACGAAGAGGAAATCAGGACAACCAATCC*
*CGTGGCTACGGAGCAGTATGGTTCTGTATCTACCAACCTCCAGAGAGGCAACGCGGCCGCCG
GGTCGACGCCGCCTCCTATG*GCGGCGCGCCAAGCAGCTACCGCAGATGTCAACACACAAGG*
*CGTTCTTCCAGGCATGGTCTGGCAGGACAGAGATGTGTACCTTCAGGGGCCCATCTGGGCAA*
*AGATTCCACACACGGACGGACATTTTCACCCCTCTCCCCTCATGGGTGGATTCGGACTTAAAC*
*ACCCTCCTCCACAGATTCTCATCAAGAACACCCCGGTACCTGCGAATCCTTCGACCACCTTCA*
*GTGCGGCAAAGTTTGCTTCCTTCATCACACAGTACTCCACGGGACAGGTCAGCGTGGAGATCG*
*AGTGGGAGCTGCAGAAGGAAAACAGCAAACGCTGGAATCCCGAAATTCAGTACACTTCCAAC*
*TACAACAAGTCTGTTAATGTGGACTTTACTGTGGACACTAATGGCGTGTATTCAGAGCCTCG*
*CCCCATTGGCACCAGATACCTGACTCGTAATCTGTAATTGCTTGTTAATCAATAAACCGTTT*
AATTCGTTTCAGTTGAACTTTGGTCTCTGCGTATTTCTTTCTTATCTAGTTTCCATGCTC
TAGAGTCCTGTATTAGAGGTCACGTGAGTGTTTTGCGACATTTTGCGACACCATGTGGTC
ACGCTGGGTATTTAAGCCCGAGTGAGCACGCAGGGTCTCCATTTTGAAGCGGGAGGTTTG
AACGCGCAGCCGCCATGCCGGGGTTTTACGAGATTGTGATTAAGGTCCCCAGCGACCTTG
ACGGGCATCTGCCCGGCATTTCTGACAGCTTTGTGAACTGGGTGGCCGAGAAGGAATGGG
AGTTGCCGCCAGATTCTGACATGGATCTGAATCTGATTGAGCAGGCACCCCTGACCGTGG
CCGAGAAGCTGCATCGCTGGCGTAATAGCGAAGAGGCCCGCACCGATCGCCCTTCCCAAC
AGTTGCGCAGCCTGAATGGCGAATGGAATTCCAGACGATTGAGCGTCAAAATGTAGGTA
TTTCCATGAGCGTTTTTCCTGTTGCAATGGCTGGCGGTAATATTGTTCTGGATATTACCA
GCAAGGCCGATAGTTTGAGTTCTTCTACTCAGGCAAGTGATGTTATTACTAATCAAAGA
AGTATTGCGACAACGGTTAATTTGCGTGATGGACAGACTCTTTTACTCGGTGGCCTCACT
GATTATAAAAACACTTCTCAGGATTCTGGCGTACCGTTCCTGTCTAAAATCCCTTTAATC

Figure 1C

GGCCTCCTGTTTAGCTCCCGCTCTGATTCTAACGAGGAAAGCACGTTATACGTGCTCGTC
AAAGCAACCATAGTACGCGCCCTGTAGCGGCGCATTAAGCGCGGCGGGTGTGGTGGTTAC
GCGCAGCGTGACCGCTACACTTGCCAGCGCCCTAGCGCCCGCTCCTTTCGCTTTCTTCCCT
TCCTTTCTCGCCACGTTCGCCGGCTTTCCCCGTCAAGCTCTAAATCGGGGGCTCCCTTTAG
GGTTCCGATTTAGTGCTTTACGGCACCTCGACCCCAAAAAACTTGATTAGGGTGATGGTT
CACGTAGTGGGCCATCGCCCTGATAGACGGTTTTTCGCCCTTTGACGTTGGAGTCCACGT
TCTTTAATAGTGGACTCTTGTTCCAAACTGGAACAACACTCAACCCTATCTCGGTCTATT
CTTTTGATTTATAAGGGATTTTGCCGATTTCGGCCTATTGGTTAAAAAATGAGCTGATT
TAACAAAAATTTAACGCGAATTTTAACAAAATATTAACGTTTACAATTTAAATATTTGC
TTATACAATCTTCCTGTTTTTGGGGCTTTTCTGATTATCAACCGGGGTACATATGATTGA
CATGCTAGTTTTACGATTACCGTTCATCGATTCTCTTGTTTGCTCCAGACTCTCAGGCAA
TGACCTGATAGCCTTTGTAGAGACCTCTCAAAAATAGCTACCCTCTCCGGCATGAATTTA
TCAGCTAGAACGGTTGAATATCATATTGATGGTGATTTGACTGTCTCCGGCCTTTCTCAC
CCGTTTGAATCTTTACCTACACATTACTCAGGCATTGCATTTAAAATATATGAGGGTTCT
AAAAATTTTTATCCTTGCGTTGAAATAAAGGCTTCTCCCGCAAAAGTATTACAGGGTCA
TAATGTTTTTGGTACAACCGATTTAGCTTTATGCTCTGAGGCTTTATTGCTTAATTTTGC
TAATTCTTTGCCTTGCCTGTATGATTTATTGGATGTTGGAATTCCTGATGCGGTATTTC
TCCTTACGCATCTGTGCGGTATTTCACACCGCATATGGTGCACTCTCAGTACAATCTGCT
CTGATGCCGCATAGTTAAGCCAGCCCCGACACCCGCCAACACCCGCTGACGCGCCCTGACG
GGCTTGTCTGCTCCCGGCATCCGCTTACAGACAAGCTGTGACCGTCTCCGGGAGCTGCAT
GTGTCAGAGGTTTTCACCGTCATCACCGAAACGCGCGAGACGAAAGGGCCTCGTGATACG
CCTATTTTTATAGGTTAATGTCATGATAATAATGGTTTCTTAGACGTCAGGTGGCACTTT
TCGGGGAAATGTGCGCGGAACCCCTATTTGTTTATTTTTCTAAATACATTCAAATATGTA
TCCGCTCATGAGACAATAACCCTGATAAATGCTTCAATAATATTGAAAAAGGAAGAGTA
TGAGTATTCAACATTTCCGTGTCGCCCTTATTCCCTTTTTTGCGGCATTTTGCCTTCCTG
TTTTTGCTCACCCAGAAACGCTGGTGAAAGTAAAAGATGCTGAAGATCAGTTGGGTGCA
CGAGTGGGTTACATCGAACTGGATCTCAACAGCGGTAAGATCCTTGAGAGTTTTCGCCCC
GAAGAACGTTTTCCAATGATGAGCACTTTTAAAGTTCTGCTATGTGGCGCGGTATTATCC
CGTATTGACGCCGGGCAAGAGCAACTCGGTCGCCGCATACACTATTCTCAGAATGACTTG
GTTGAGTACTCACCAGTCACAGAAAAGCATCTTACGGATGGCATGACAGTAAGAGAATT
ATGCAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTCGCCT
TGATCGTTGGGAACCGGAGCTGAATGAAGCCATACCAAACGACGAGCGTGACACCACGAT
GCCTGTAGCAATGGCAACAACGTTGCGCAAACTATTAACTGGCGAACTACTTACTCTAGC
TTCCCGGCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTA
CACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTG
ATTTAAAACTTCATTTTTAATTTAAAAGGATCTAGGTGAAGATCCTTTTTGATAATCTC
ATGACCAAAATCCCTTAACGTGAGTTTTCGTTCCACTGAGCGTCAGACCCCGTAGAAAAG
ATCAAAGGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCTTTTTCCG
AAGGTAACTGGCTTCAGCAGAGCGCAGATACCAAATACTGTCCTTCTAGTGTAGCCGTAG

Figure 1D

TTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAGC
TTGGAGCGAACGACCTACACCGAACTGAGATACCTACAGCGTGAGCTATGAGAAAGCGCC
ACGCTTCCCGAAGGGAGAAAGGCGGACAGGTATCCGGTAAGCGGCAGGGTCGGAACAGG
AGAGCGCACGAGGGAGCTTCCAGGGGGAAACGCCTGGTATCTTTATAGTCCTGTCGGGTT
TCGCCACCTCTGACTTGAGCGTCGATTTTTGTGATGCTCGTCAGGGGGGCGGAGCCTATG
GAAAAACGCCAGCAACGCGGCCTTTTTACGGTTCCTGGCCTTTTGCTGGCCTTTTGCTCA
CATGTTCTTTCCTGCGTTATCCCCTGATTCTGTGGATAACCGTATTACCGCCTTTGAGTG
AGCTGATACCGCTCGCCGCAGCCGAACGACCGAGCGCAGCGAGTCAGTGAGCGAGGAAGC
GGAAGAGCGCCCAATACGCAAACCGCCTCTCCCCGCGCGTTGGCCGATTCATTAATGCAG
(SEQ ID NO:3)

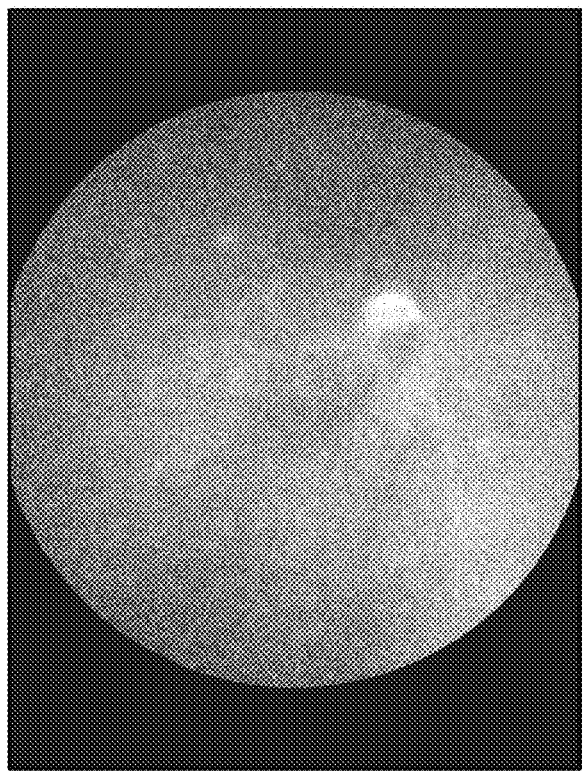
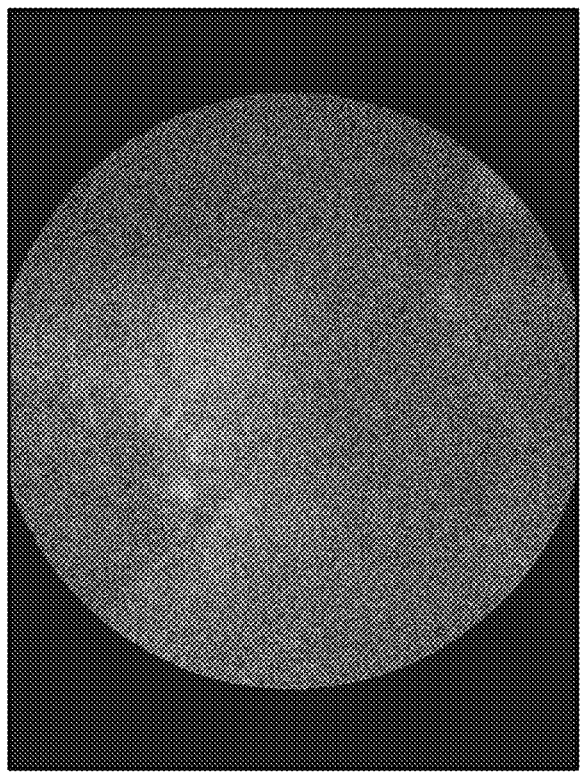
Figure 2

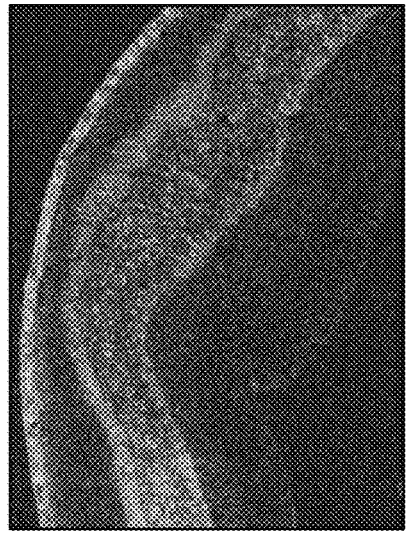
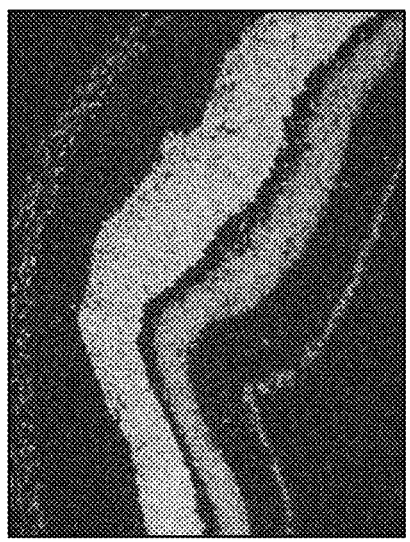
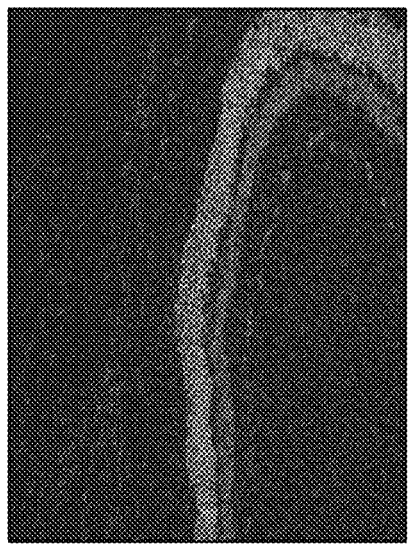
Figure 3

Subretinal injections

Intravitreal injections

AAV2 Intravitreal injections
ONL
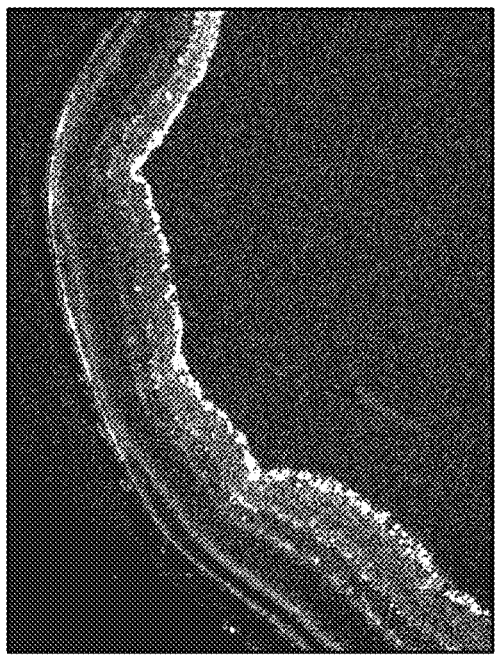
Figure 9

AAV2 PM GST Intravitreal injections

```
                            SEQUENCE LISTING

<160> NUMBER OF SEQ ID NOS: 11

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Ser Thr Pro Pro Pro Met
1               5

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gggtcgacgc cgcctcctat g                                                 21

<210> SEQ ID NO 3
<211> LENGTH: 8413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
aattcccatc atcaataata taccttattt tggattgaag ccaatatgat aatgaggggg       60
tggagtttgt gacgtggcgc ggggcgtggg aacggggcgg gtgacgtagt agtctctaga      120
gtcctgtatt agaggtcacg tgagtgtttt gcgacatttt gcgacaccat gtggtcacgc      180
tgggtattta agcccgagtg agcacgcagg gtctccattt tgaagcggga ggtttgaacg      240
cgcagccgcc atgccggggt tttacgagat tgtgattaag gtccccagcg accttgacgg      300
gcatctgccc ggcatttctg acagctttgt gaactgggtg gccgagaagg aatgggagtt      360
gccgccagat tctgacatgg atctgaatct gattgagcag gcacccctga ccgtggccga      420
gaagctgcag cgcgactttc tgacggaatg gcgccgtgtg agtaaggccc cggaggccct      480
```

```
tttctttgtg caatttgaga agggagagag ctacttccac atgcacgtgc tcgtggaaac      540
caccggggtg aaatccatgg ttttgggacg tttcctgagt cagattcgcg aaaaactgat      600
tcagagaatt taccgcggga tcgagccgac tttgccaaac tggttcgcgg tcacaaagac      660
cagaaatggc gccggaggcg ggaacaaggt ggtggatgag tgctacatcc ccaattactt      720
gctccccaaa acccagcctg agctccagtg ggcgtggact aatatggaac agtatttaag      780
cgcctgtttg aatctcacgg agcgtaaacg gttggtggcg cagcatctga cgcacgtgtc      840
gcagacgcag gagcagaaca aagagaatca gaatcccaat tctgatgcgc cggtgatcag      900
atcaaaaact tcagccaggt acatggagct ggtcgggtgg ctcgtggaca agggattac       960
ctcggagaag cagtggatcc aggaggacca ggcctcatac atctccttca atgcggcctc     1020
caactcgcgg tcccaaatca aggctgcctt ggacaatgcg ggaaagatta tgagcctgac     1080
taaaaccgcc cccgactacc tggtgggcca gcagcccgtg gaggacattt ccagcaatcg     1140
gatttataaa attttggaac taaacgggta cgatccccaa tatgcggctt ccgtctttct     1200
gggatgggcc acgaaaaagt tcggcaagag gaacaccatc tggctgtttg ggcctgcaac     1260
taccgggaag accaacatcg cggaggccat agcccacact gtgcccttct acgggtgcgt     1320
aaactggacc aatgagaact tcccttcaa cgactgtgtc gacaagatgg tgatctggtg      1380
ggaggagggg aagatgaccg ccaaggtcgt ggagtcggcc aaagccattc tcggaggaag     1440
caaggtgcgc gtgaccagaa atgcaagtc ctcggcccag atagacccga ctcccgtgat      1500
cgtcacctcc aacaccaaca tgtgcgccgt gattgacggg aactcaacga ccttcgaaca     1560
ccagcagccg ttgcaagacc ggatgttcaa atttgaactc acccgccgtc tggatcatga     1620
ctttgggaag gtcaccaagc aggaagtcaa agacttttc cggtgggcaa aggatcacgt      1680
ggttgaggtg gagcatgaat tctacgtcaa aaagggtgga gccaagaaaa gacccgcccc     1740
cagtgacgca gatataagtg agcccaaacg ggtgcgcgag tcagttgcgc agccatcgac     1800
gtcagacgcg gaagcttcga tcaactacgc agacaggtac caaaacaaat gttctcgtca     1860
cgtgggcatg aatctgatgc tgtttccctg cagacaatgc gagagaatga atcagaattc     1920
aaatatctgc ttcactcacg gacagaaaga ctgtttagag tgctttcccg tgtcagaatc     1980
tcaacccgtt tctgtcgtca aaaaggcgta tcagaaactg tgctacattc atcatatcat     2040
gggaaaggtg ccagacgctt gcactgcctg cgatctggtc aatgtggatt tggatgactg     2100
catctttgaa caataaatga tttaaatcag gtatggctgc cgatggttat cttccagatt     2160
ggctcgagga cactctctct gaaggaataa gacagtggtg gaagctcaaa cctggcccac     2220
caccaccaaa gcccgcagag cggcataagg acgacagcag gggtcttgtg cttcctgggt     2280
acaagtacct cggaccctttc aacgactcg caagggaga gccggtcaac gaggcagacg      2340
ccgcggccct cgagcacgac aaagcctacg accggcagct cgacagcgga gacaacccgt     2400
acctcaagta caaccacgcc gacgcggagt ttcaggagcg ccttaaagaa gatacgtctt     2460
ttgggggcaa cctcggacga gcagtcttcc aggcgaaaaa gagggttctt gaacctctgg     2520
gcctggttga ggaacctgtt aagacggctc cgggaaaaaa gaggccggta gagcactctc     2580
ctgtggagcc agactcctcc tcgggaaccg gaaaggcggg ccagcagcct gcaagaaaaa     2640
gattgaattt tggtcagact ggagacgcag actcagtacc tgaccccag cctctcggac      2700
agccaccagc agccccctct ggtctgggaa ctaatacgat ggctacaggc agtggcgcac     2760
caatggcaga caataacgag ggcgccgacg gagtgggtaa ttcctcggga aattggcatt     2820
gcgattccac atggatgggc gacagagtca tcaccaccag cacccgaacc tgggccctgc     2880
```

```
ccacctacaa caaccacctc tacaaacaaa tttccagcca atcaggagcc tcgaacgaca    2940
atcactactt tggctacagc accccttggg ggtattttga cttcaacaga ttccactgcc    3000
acttttcacc acgtgactgg caaagactca tcaacaacaa ctggggattc cgacccaaga    3060
gactcaactt caagctcttt aacattcaag tcaaagaggt cacgcagaat gacggtacga    3120
cgacgattgc caataacctt accagcacgg ttcaggtgtt tactgactcg gagtaccagc    3180
tcccgtacgt cctcggctcg gcgcatcaag gatgcctccc gccgttccca gcagacgtct    3240
tcatggtgcc acagtatgga tacctcaccc tgaacaacgg gagtcaggca gtaggacgct    3300 cttcattta ctgcctggag tactttcctt ctcagatgct gcgtaccgga aacaacttta     3360
ccttcagcta cacttttgag gacgttcctt tccacagcag ctacgctcac agccagagtc    3420
tggaccgtct catgaatcct ctcatcgacc agtacctgta ttacttgagc agaacaaaca    3480
ctccaagtgg aaccaccacg cagtcaaggc ttcagttttc tcaggccgga gcgagtgaca    3540
ttcgggacca gtctaggaac tggcttcctg gaccctgtta ccgccagcag cgagtatcaa    3600
agacatctgc ggataacaac aacagtgaat actcgtggac tggagctacc aagtaccacc    3660
tcaatggcag agactctctg gtgaatccgg gcccggccat ggcaagccac aaggacgatg    3720
aagaaaagtt ttttcctcag agcggggttc tcatctttgg gaagcaaggc tcagagaaaa    3780
caaatgtgga cattgaaaag gtcatgatta cagacgaaga ggaaatcagg acaaccaatc    3840
ccgtggctac ggagcagtat ggttctgtat ctaccaacct ccagagaggc aacgcggccg    3900
ccgggtcgac gccgcctcct atggcggcgc gccaagcagc taccgcagat gtcaacacac    3960
aaggcgttct tccaggcatg gtctggcagg acagagatgt gtaccttcag gggcccatct    4020
gggcaaagat tccacacacg gacggacatt ttcacccctc tcccctcatg ggtggattcg    4080
gacttaaaca ccctcctcca cagattctca tcaagaacac cccggtacct gcgaatcctt    4140
cgaccacctt cagtgcggca aagtttgctt ccttcatcac acagtactcc acggacagg    4200 tcagcgtgga gatcgagtgg gagctgcaga aggaaaacag caaacgctgg aatcccgaaa    4260
ttcagtacac ttccaactac aacaagtctg ttaatgtgga ctttactgtg gacactaatg    4320
gcgtgtattc agagcctcgc cccattggca ccagatacct gactcgtaat ctgtaattgc    4380
ttgttaatca ataaaccgtt taattcgttt cagttgaact ttggtctctg cgtatttctt    4440
tcttatctag tttccatgct ctagagtcct gtattagagg tcacgtgagt gttttgcgac    4500
attttgcgac accatgtggt cacgctgggt atttaagccc gagtgagcac gcagggtctc    4560
cattttgaag cgggaggttt gaacgcgcag ccgccatgcc ggggttttac gagattgtga    4620
ttaaggtccc cagcgacctt gacgggcatc tgcccggcat ttctgacagc tttgtgaact    4680
gggtggccga gaaggaatgg gagttgccgc cagattctga catggatctg aatctgattg    4740
agcaggcacc cctgaccgtg gccgagaagc tgcatcgctg gcgtaatagc gaagaggccc    4800
gcaccgatcg cccttcccaa cagttgcgca gcctgaatgg cgaatggaat tccagacgat    4860
tgagcgtcaa aatgtaggta tttccatgag cgttttcct gttgcaatgg ctggcggtaa     4920
tattgttctg gatattacca gcaaggccga tagtttgagt tcttctactc aggcaagtga    4980
tgttattact aatcaaagaa gtattgcgac aacggttaat ttgcgtgatg acagactct     5040 tttactcggt ggcctcactg attataaaaa cacttctcag gattctggcg taccgttcct    5100
gtctaaaatc cctttaatcg gcctcctgtt tagctcccgc tctgattcta acgaggaaag    5160
cacgttatac gtgctcgtca aagcaaccat agtacgcgcc ctgtagcggc gcattaagcg    5220
```

```
cggcgggtgt ggtggttacg cgcagcgtga ccgctacact tgccagcgcc ctagcgcccg    5280
ctcctttcgc tttcttccct tcctttctcg ccacgttcgc cggctttccc cgtcaagctc    5340
taaatcgggg gctcccttta gggttccgat ttagtgcttt acggcacctc gaccccaaaa    5400
aacttgatta gggtgatggt tcacgtagtg ggcatcgcc ctgatagacg ttttttcgcc     5460
ctttgacgtt ggagtccacg ttctttaata gtggactctt gttccaaact ggaacaacac    5520
tcaaccctat ctcggtctat tcttttgatt tataagggat tttgccgatt tcggcctatt    5580
ggttaaaaaa tgagctgatt taacaaaaat ttaacgcgaa ttttaacaaa atattaacgt    5640
ttacaattta aatatttgct tatacaatct tcctgttttt ggggcttttc tgattatcaa    5700
ccggggtaca tatgattgac atgctagttt tacgattacc gttcatcgat tctcttgttt    5760
gctccagact ctcaggcaat gacctgatag cctttgtaga gacctctcaa aaatagctac    5820
cctctccggc atgaatttat cagctagaac ggttgaatat catattgatg gtgatttgac    5880
tgtctccggc ctttctcacc cgtttgaatc tttacctaca cattactcag gcattgcatt    5940
taaaatatat gagggttcta aaaatttta tccttgcgtt gaaataaagg cttctcccgc     6000
aaaagtatta cagggtcata atgtttttgg tacaaccgat ttagctttat gctctgaggc    6060
tttattgctt aattttgcta attctttgcc ttgcctgtat gatttattgg atgttggaat    6120
tcctgatgcg gtattttctc cttacgcatc tgtgcggtat ttcacaccgc atatggtgca    6180
ctctcagtac aatctgctct gatgccgcat agttaagcca gccccgacac cgccaacac     6240 ccgctgacgc gccctgacgg gcttgtctgc tcccggcatc cgcttacaga caagctgtga    6300
ccgtctccgg gagctgcatg tgtcagaggt tttcaccgtc atcaccgaaa cgcgcgagac    6360
gaaagggcct cgtgatacgc ctatttttat aggttaatgt catgataata atggtttctt    6420
agacgtcagg tggcactttt cggggaaatg tgcgcggaac ccctatttgt ttattttct     6480 aaatacattc aaatatgtat ccgctcatga caataaacc ctgataaatg cttcaataat     6540
attgaaaaag gaagagtatg agtattcaac atttccgtgt cgcccttatt ccctttttg     6600 cggcattttg ccttcctgtt tttgctcacc cagaaacgct ggtgaaagta aaagatgctg    6660
aagatcagtt gggtgcacga gtgggttaca tcgaactgga tctcaacagc ggtaagatcc    6720
ttgagagttt tcgccccgaa gaacgttttc caatgatgag cacttttaaa gttctgctat    6780
gtggcgcggt attatcccgt attgacgccg ggcaagagca actcggtcgc cgcatacact    6840
attctcagaa tgacttggtt gagtactcac cagtcacaga aaagcatctt acggatggca    6900
tgacagtaag agaattatgc agtgctgcca taaccatgag tgataacact gcggccaact    6960
tacttctgac aacgatcgga ggaccgaagg agctaaccgc ttttttgcac aacatggggg    7020
atcatgtaac tcgccttgat cgttgggaac cggagctgaa tgaagccata ccaaacgacg    7080
agcgtgacac cacgatgcct gtagcaatgg caacaacgtt gcgcaaacta ttaactggcg    7140
aactacttac tctagcttcc cggcaacaat taatagactg gatggaggcg gataaagttg    7200
caggaccact tctgcgctcg gcccttccgg ctggctggtt tattgctgat aaatctggag    7260
ccggtgagcg tgggtctcgc ggtatcattg cagcactggg gccagatggt aagccctccc    7320
gtatcgtagt tatctacacg acggggagtc aggcaactat ggatgaacga atagacaga    7380 tcgctgagat aggtgcctca ctgattaagc attggtaact gtcagaccaa gtttactcat    7440
atatacttta gattgattta aaacttcatt tttaatttaa aaggatctag gtgaagatcc    7500
tttttgataa tctcatgacc aaaatccctt aacgtgagtt ttcgttccac tgagcgtcag    7560
accccgtaga aaagatcaaa ggatcttctt gagatccttt ttttctgcgc gtaatctgct    7620
```

-continued

```
gcttgcaaac aaaaaaacca ccgctaccag cggtggtttg tttgccggat caagagctac    7680 caactcttt  tccgaaggta actggcttca gcagagcgca gataccaaat actgtccttc    7740
tagtgtagcc gtagttaggc caccacttca agaactctgt agcaccgcct acatacctcg    7800
ctctgctaat cctgttacca gtggctgctg ccagtggcga taagtcgtgt cttaccgggt    7860
tggactcaag acgatagtta ccggataagg cgcagcggtc gggctgaacg ggggggttcgt    7920 gcacacagcc cagcttggag cgaacgacct acaccgaact gagataccta cagcgtgagc    7980
tatgagaaag cgccacgctt cccgaaggga gaaaggcgga caggtatccg gtaagcggca    8040
gggtcggaac aggagagcgc acgagggagc ttccagggg  aaacgcctgg tatctttata    8100
gtcctgtcgg gtttcgccac ctctgacttg agcgtcgatt tttgtgatgc tcgtcagggg    8160
ggcggagcct atggaaaaac gccagcaacg cggcctttt  acggttcctg gccttttgct    8220
ggccttttgc tcacatgttc tttcctgcgt tatcccctga ttctgtggat aaccgtatta    8280
ccgcctttga gtgagctgat accgctcgcc gcagccgaac gaccgagcgc agcgagtcag    8340
tgagcgagga agcggaagag cgcccaatac gcaaaccgcc tctccccgcg cgttggccga    8400
ttcattaatg cag                                                      8413
```

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Glu Thr Arg Ala Pro Leu
1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Met Pro Pro Pro Thr Ser Gly
1               5

<210> SEQ ID NO 6
<211> LENGTH: 18
<212> TYPE: DNA
<213> ORGANISM: Adeno-associated virus 2
<220> FEATURE:
<221> NAME/KEY: CDS
<222> LOCATION: (1)..(18)

<400> SEQUENCE: 6 aga ggc aac aga caa gca                                             18
Arg Gly Asn Arg Gln Ala
1               5

<210> SEQ ID NO 7
<211> LENGTH: 6
<212> TYPE: PRT
<213> ORGANISM: Adeno-associated virus 2

<400> SEQUENCE: 7

Arg Gly Asn Arg Gln Ala
1               5

<210> SEQ ID NO 8
<211> LENGTH: 735
<212> TYPE: PRT
<213> ORGANISM: Adeno-associated virus 2

<400> SEQUENCE: 8

Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp

```
            355                 360                 365
Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
                420                 425                 430

Leu Met Asn Pro Leu Ile Asp Gln Tyr Leu Tyr Tyr Leu Ser Arg Thr
            435                 440                 445

Asn Thr Pro Ser Gly Thr Thr Thr Gln Ser Arg Leu Gln Phe Ser Gln
        450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Arg Gln Ala Ala Thr
            580                 585                 590

Ala Asp Val Asn Thr Gln Gly Val Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Leu Ile Lys Asn Thr Pro Val Pro Ala Asn
                645                 650                 655

Pro Ser Thr Thr Phe Ser Ala Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Asn Leu
                725                 730                 735

<210> SEQ ID NO 9
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 9

```
Met Ala Ala Asp Gly Tyr Leu Pro Asp Trp Leu Glu Asp Thr Leu Ser
1               5                   10                  15

Glu Gly Ile Arg Gln Trp Trp Lys Leu Lys Pro Gly Pro Pro Pro Pro
            20                  25                  30

Lys Pro Ala Glu Arg His Lys Asp Asp Ser Arg Gly Leu Val Leu Pro
        35                  40                  45

Gly Tyr Lys Tyr Leu Gly Pro Phe Asn Gly Leu Asp Lys Gly Glu Pro
50                  55                  60

Val Asn Glu Ala Asp Ala Ala Ala Leu Glu His Asp Lys Ala Tyr Asp
65                  70                  75                  80

Arg Gln Leu Asp Ser Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Pro Val Lys Thr Ala Pro Gly Lys Lys Arg
130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
```

405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
            485                 490                 495

Asn Ser Glu Tyr Ser Trp Thr Gly Ala Thr Lys Tyr His Leu Asn Gly
        500                 505                 510

Arg Asp Ser Leu Val Asn Pro Gly Pro Ala Met Ala Ser His Lys Asp
    515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Ala Ala Ala Gly Ser
            580                 585                 590

Thr Pro Pro Pro Met Ala Ala Arg Gln Ala Ala Thr Ala Asp Val Asn
        595                 600                 605

Thr Gln Gly Val Leu Pro Gly Met Val Trp Gln Asp Arg Asp Val Tyr
    610                 615                 620

Leu Gln Gly Pro Ile Trp Ala Lys Ile Pro His Thr Asp Gly His Phe
625                 630                 635                 640

His Pro Ser Pro Leu Met Gly Gly Phe Gly Leu Lys His Pro Pro Pro
                645                 650                 655

Gln Ile Leu Ile Lys Asn Thr Pro Val Pro Ala Asn Pro Ser Thr Thr
            660                 665                 670

Phe Ser Ala Ala Lys Phe Ala Ser Phe Ile Thr Gln Tyr Ser Thr Gly
        675                 680                 685

Gln Val Ser Val Glu Ile Glu Trp Glu Leu Gln Lys Glu Asn Ser Lys
    690                 695                 700

Arg Trp Asn Pro Glu Ile Gln Tyr Thr Ser Asn Tyr Asn Lys Ser Val
705                 710                 715                 720

Asn Val Asp Phe Thr Val Asp Thr Asn Gly Val Tyr Ser Glu Pro Arg
                725                 730                 735

Pro Ile Gly Thr Arg Tyr Leu Thr Arg Asn Leu
            740                 745

<210> SEQ ID NO 10
<211> LENGTH: 747
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Ala Ala Asp Gly Tyr Leu Pro Asp Trp Leu Glu Asp Thr Leu Ser
1               5                   10                  15

-continued

```
Glu Gly Ile Arg Gln Trp Trp Lys Leu Lys Pro Gly Pro Pro Pro
            20              25              30
Lys Pro Ala Glu Arg His Lys Asp Asp Ser Arg Gly Leu Val Leu Pro
        35              40              45
Gly Tyr Lys Tyr Leu Gly Pro Phe Asn Gly Leu Asp Lys Gly Glu Pro
        50              55              60
Val Asn Glu Ala Asp Ala Ala Ala Leu Glu His Asp Lys Ala Tyr Asp
65              70              75              80
Arg Gln Leu Asp Ser Gly Asp Asn Pro Tyr Leu Lys Tyr Asn His Ala
                85              90              95
Asp Ala Glu Phe Gln Glu Arg Leu Lys Glu Asp Thr Ser Phe Gly Gly
            100             105             110
Asn Leu Gly Arg Ala Val Phe Gln Ala Lys Lys Arg Val Leu Glu Pro
        115             120             125
Leu Gly Leu Val Glu Glu Pro Val Lys Thr Ala Pro Gly Lys Lys Arg
        130             135             140
Pro Val Glu His Ser Pro Val Glu Pro Asp Ser Ser Gly Thr Gly
145             150             155             160
Lys Ala Gly Gln Gln Pro Ala Arg Lys Arg Leu Asn Phe Gly Gln Thr
                165             170             175
Gly Asp Ala Asp Ser Val Pro Asp Pro Gln Pro Leu Gly Gln Pro Pro
            180             185             190
Ala Ala Pro Ser Gly Leu Gly Thr Asn Thr Met Ala Thr Gly Ser Gly
        195             200             205
Ala Pro Met Ala Asp Asn Asn Glu Gly Ala Asp Gly Val Gly Asn Ser
        210             215             220
Ser Gly Asn Trp His Cys Asp Ser Thr Trp Met Gly Asp Arg Val Ile
225             230             235             240
Thr Thr Ser Thr Arg Thr Trp Ala Leu Pro Thr Tyr Asn Asn His Leu
                245             250             255
Tyr Lys Gln Ile Ser Ser Gln Ser Gly Ala Ser Asn Asp Asn His Tyr
            260             265             270
Phe Gly Tyr Ser Thr Pro Trp Gly Tyr Phe Asp Phe Asn Arg Phe His
        275             280             285
Cys His Phe Ser Pro Arg Asp Trp Gln Arg Leu Ile Asn Asn Asn Trp
    290             295             300
Gly Phe Arg Pro Lys Arg Leu Asn Phe Lys Leu Phe Asn Ile Gln Val
305             310             315             320
Lys Glu Val Thr Gln Asn Asp Gly Thr Thr Thr Ile Ala Asn Asn Leu
                325             330             335
Thr Ser Thr Val Gln Val Phe Thr Asp Ser Glu Tyr Gln Leu Pro Tyr
            340             345             350
Val Leu Gly Ser Ala His Gln Gly Cys Leu Pro Pro Phe Pro Ala Asp
        355             360             365
Val Phe Met Val Pro Gln Tyr Gly Tyr Leu Thr Leu Asn Asn Gly Ser
    370             375             380
Gln Ala Val Gly Arg Ser Ser Phe Tyr Cys Leu Glu Tyr Phe Pro Ser
385             390             395             400
Gln Met Leu Arg Thr Gly Asn Asn Phe Thr Phe Ser Tyr Thr Phe Glu
                405             410             415
Asp Val Pro Phe His Ser Ser Tyr Ala His Ser Gln Ser Leu Asp Arg
            420             425             430
Leu Met Asn Pro Leu Ile Asp Gln Tyr Leu Tyr Tyr Leu Ser Arg Thr
```

```
                435                 440                 445
Asn Thr Pro Ser Gly Thr Thr Thr Gln Ser Arg Leu Gln Phe Ser Gln
450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
530                 535                 540

Gln Gly Ser Glu Lys Thr Asn Val Asp Ile Glu Lys Val Met Ile Thr
545                 550                 555                 560

Asp Glu Glu Glu Ile Arg Thr Thr Asn Pro Val Ala Thr Glu Gln Tyr
                565                 570                 575

Gly Ser Val Ser Thr Asn Leu Gln Arg Gly Asn Ala Ala Ala Gly Glu
            580                 585                 590

Thr Arg Ala Pro Leu Ala Ala Arg Gln Ala Ala Thr Ala Asp Val Asn
        595                 600                 605

Thr Gln Gly Val Leu Pro Gly Met Val Trp Gln Asp Arg Asp Val Tyr
610                 615                 620

Leu Gln Gly Pro Ile Trp Ala Lys Ile Pro His Thr Asp Gly His Phe
625                 630                 635                 640

His Pro Ser Pro Leu Met Gly Gly Phe Gly Leu Lys His Pro Pro Pro
                645                 650                 655

Gln Ile Leu Ile Lys Asn Thr Pro Val Pro Ala Asn Pro Ser Thr Thr
            660                 665                 670

Phe Ser Ala Ala Lys Phe Ala Ser Phe Ile Thr Gln Tyr Ser Thr Gly
        675                 680                 685

Gln Val Ser Val Glu Ile Glu Trp Glu Leu Gln Lys Glu Asn Ser Lys
690                 695                 700

Arg Trp Asn Pro Glu Ile Gln Tyr Thr Ser Asn Tyr Asn Lys Ser Val
705                 710                 715                 720

Asn Val Asp Phe Thr Val Asp Thr Asn Gly Val Tyr Ser Glu Pro Arg
                725                 730                 735

Pro Ile Gly Thr Arg Tyr Leu Thr Arg Asn Leu
            740                 745

<210> SEQ ID NO 11
<211> LENGTH: 736
<212> TYPE: PRT
<213> ORGANISM: Adeno-associated virus 9

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60
```

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn

```
                      485                 490                 495
Asn Asn Ser Glu Phe Ala Trp Pro Gly Ala Ser Ser Trp Ala Leu Asn
                500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
        530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735
```

METHODS AND COMPOSITIONS FOR TREATING GENETIC EYE DISEASES

RELATED APPLICATION

This application claims priority to U.S. Provisional Application No. 62/118,934, filed Feb. 20, 2015, the entirety of which is incorporated herein by reference.

SEQUENCE LISTING

The instant application contains a Sequence Listing which has been submitted in ASCII format via EFS-Web and is hereby incorporated by reference in its entirety. Said ASCII copy, created on Mar. 8, 2016, is named 17023_145WO1_SL.txt and is 38,489 bytes in size.

INTRODUCTION

Gene transfer is now widely recognized as a powerful tool for analysis of biological events and disease processes at both the cellular and molecular levels. Recently, the application of gene therapy for the treatment of human diseases, either inherited (e.g., adenosine deaminase (ADA) deficiency) or acquired (e.g., cancer or infectious disease), has received considerable attention. With the advent of improved gene transfer techniques and the identification of an ever expanding library of defective gene-related diseases, gene therapy has rapidly evolved from a treatment theory to a practical reality.

Traditionally, gene therapy has been defined as a procedure in which an exogenous gene is introduced into the cells of a patient in order to correct an inborn genetic error. Although more than 4500 human diseases are currently classified as genetic, specific mutations in the human genome have been identified for relatively few of these diseases. Until recently, these rare genetic diseases represented the exclusive targets of gene therapy efforts. Accordingly, most of the NIH approved gene therapy protocols to date have been directed toward the introduction of a functional copy of a defective gene into the somatic cells of an individual having a known inborn genetic error. Only recently, have researchers and clinicians begun to appreciate that most human cancers, certain forms of cardiovascular disease, and many degenerative diseases also have important genetic components, and for the purposes of designing novel gene therapies, should be considered "genetic disorders." Therefore, gene therapy has more recently been broadly defined as the correction of a disease phenotype through the introduction of new genetic information into the affected organism.

In in vivo gene therapy, a transferred gene is introduced into cells of the recipient organism in situ that is, within the recipient. In vivo gene therapy has been examined in several animal models. Several recent publications have reported the feasibility of direct gene transfer in situ into organs and tissues such as muscle, hematopoietic stem cells, the arterial wall, the nervous system, and lung. Direct injection of DNA into skeletal muscle, heart muscle and injection of DNA-lipid complexes into the vasculature also has been reported to yield a detectable expression level of the inserted gene product(s) in vivo.

Treatment of genetic diseases of the eye, e.g., inherited genetic diseases of the eye, such as diseases that cause blindness, remains a problem. Examples of such are retinitis pigmentosa, maculopathies, Leber's congenital amaurosis, Leber's hereditary optic neuropathy, early onset severe retinal dystrophy, achromatopsia, retinoschisis, ocular albinism, oculocutaneous albinism, glaucoma, Stargardt disease, choroideremia, age-related macular degeneration, Spinocerebellar Ataxia Type 7 (SCAT), color blindness, and lysosomal storage diseases that affect the cornea, such as Mucopolysaccharidosis (MPS) IV and MPS VII. Thus, therapies for genetic diseases of the eye need to be developed.

SUMMARY

The present inventors have discovered peptides that function to target agents, such as viral vectors, to ocular cells. The present disclosure describes a method to utilize these novel peptides to direct, for example, viral capsids to the cell type of interest. In this instance, ocular cells (such as retinal cells) are targeted by the identified peptides. Vectors harboring capsid proteins modified to include such peptides can be used to provide therapeutic agents to the eye.

As used herein, the term "targets" means that the capsid protein of a virus, such as an adeno-associated virus (AAV), preferentially binds to one type of tissue (e.g., retinal cells) over another type of tissue (e.g., brain tissue) In certain embodiments, the genetically modified capsid protein may "target" ocular cells by binding at level of 10% to 1000% higher than a comparable, unmodified capsid protein. For example, an AAV having a genetically-modified capsid protein may bind to ocular cells at a level 50% to 100% greater than an unmodified AAV virus.

The present invention provides a modified adeno-associated virus (AAV) capsid protein containing a targeting peptide, wherein the targeting peptide is from 3 to 10 amino acids (i.e., 3, 4, 5, 6, 7, 8, 9, or 10 amino acids) in length and wherein the targeting peptide targets an AAV to an ocular cell. In certain embodiments, the targeting peptide is 3, 4, 5, 6, 7, 8, 9 or 10 amino acids in length.

The present invention provides an AAV virus containing the capsid protein modified genetically to encode the peptides described hereinabove.

The present invention provides a method of treating disease (e.g., an ocular disease) in a mammal by administering the viral vector described hereinabove or the cell described hereinabove to the mammal. In certain embodiments, the mammal is human. In certain embodiments, the disease is retinitis pigmentosa, maculopathies, Leber's congenital amaurosis, Leber's hereditary optic neuropathy, early onset severe retinal dystrophy, achromatopsia, retinoschisis, ocular albinism, oculocutaneous albinism, glaucoma, Stargardt disease, choroideremia, age-related macular degeneration, SCAT, color blindness, and lysosomal storage diseases that affect the cornea, such as MPS IV and MPS VII.

In certain embodiments, the disease is a lysosomal storage disease or disorder. In certain embodiments, the disease is a deficiency or defect in TPP1 (tripeptidyl peptidase I), CLN3 (Battenin), PPT1 (palmitoyl protein thioesterase I), CLN6 (neuronal ceroid lipofuscinosis protein 6) or CLN8 expression or activity. In certain embodiments, the disease is a neurodegenerative disease such as neuronal ceroid lipofuscinosis (NCL), such as infantile NCL, late infantile NCL, juvenile NCL (Batten disease) and adult NCL.

The present invention provides a method to deliver an agent to the eye of a subject, by transducing ocular cells with a viral vector described hereinabove so that the transduced ocular cells express the therapeutic agent and deliver the agent to the eye of the subject. In certain embodiments, the agent is Ataxin 7 mirRNA (for example to treat SCA 7). In certain embodiments, the agent is Retinal Pigment Epithelium-specific 65 kDa protein (RPE 65) (for example to treat Leber's congenital amaurosis). In certain embodiments, the agent is Vascular Endothelial Growth Factor (VEGF) inhibitor or soluble VEGF receptor 1 (sFif1) (for example to treat age related macular degeneration). In certain embodiments, the agent is REP1 (for example to treat Choroideremia). In certain embodiments, the agent is L-opsin (for example to treat color blindness). Table 1 sets forth exemplary diseases, target genes and corresponding encoded proteins.

TABLE 1

| Condition to be Treated | Target Gene for gene therapy | Protein Encoded |
| --- | --- | --- |
| Retinitis Pigmentosa | Rho | Rhodopsin |
| | PDE6β | Phosphodiesterase 6β |
| | ABCA4 | ATP-binding cassette, sub-family A, member 4 |
| | RPE65 | Retinal pigment epithelium-specific 65 kDa protein |
| | LRAT | Lecithin Retinol Acyltransferase |
| | RDS/Peripherin | Retinal degeneration, slow/Peripherin |
| | MERTK | Tyrosine-protein kinase Mer |
| | IMPDHI | Inosine-5-prime-monophosphate dehydrogenase, type I |
| Maculopathies | GUCY2D | Guanylate Cyclase 2D |
| | RDS/Peripherin | Retinal degeneration, slow/Peripherin |
| | AIPL1 | Aryl-hydrocarbon interacting protein-like 1 |
| | ABCA4 | ATP-binding cassette, sub-family A, member 4 |
| | RPGRIP1 | Retinitis pigmentosa GTPase regulator interacting protein 1 |
| Leber's congenital amaurosis and early onset severe retinal dystrophy | IMPDH1 | Inosine-5-prime-monophosphate dehydrogenase, type I |
| | AIPL1 | Aryl-hydrocarbon interacting protein-like 1 |
| | GUCY2D | Guanylate Cyclase 2D |
| | LRAT | Lecithin Retinol Acyltransferase |
| | MERTK | Tyrosine-protein kinase Mer |
| | RPGRIP1 | Retinitis pigmentosa GTPase regulator interacting protein 1 |
| | RPE65 | Retinal pigment epithelium-specific 65 kDa protein |
| Leber's hereditary optic neuropathy | Mitochondria Complex I genes, ND1, ND4, ND6, etc. | NADH Dehydrogenase, Subunit 1, NADH Dehydrogenase, Subunit 4, NADH Dehydrogenase, Subunit 6 |
| Stargardt disease | ABCA4 | ATP-binding cassette, sub-family A, member 4 |
| Achromatopsia | GNAT2 | Guanine nucleotide binding protein, alpha transducing activity polypeptide 2 |
| | CNGB3 | Cyclic nucleotide gated channel beta 3 |
| X-linked retinoschisis | Rsl | Retinoschisin 1 |
| Ocular albinism | OA1 | Ocular albinism type 1 |
| Oculocutaneous albinism | (OCA1) tyrosinase | Oculocutaneous albinism type 1 tyrosinase |
| Glaucoma | p21 WAF-1/0Cip 1 | Cyclin-dependent kinase inhibitor interacting protein 1 |
| Choroideremia | REP-1 | Rab escort protein-1 |
| Age related macular degeneration | PDGF | Platelet-derived growth factor |
| | Endostatin | |
| | Angiostatin | |
| | VEGF inhibitor | Vascular endothelial growth factor inhibitor |
| SCA7 | Ataxin 7 mirRNA | |
| Color blindness | Opsin | Opsin |
| Lysosomal storage disease IV | arylsulfatase B | Arylsulfatase B |
| Lysosomal storage disease VII | β-glucuronidase | β-Glucuronidase |

BRIEF DESCRIPTION OF THE DRAWINGS

FIGS. 1A-1D. Sequence of peptide modified AAV (PMAAV)-GST (SEQ ID NO: 3). AAV2/2 (AAV2 ITR/AAV2 capsid) capsid sequence (Italicized) and glutathione S-transferase (GST) retina target peptide (Bold and underlined).

FIG. 2. Fluorescent imaging in live animals showed relative infection efficiencies. Speckled regions of green fluorescent protein (GFP) positivity were observed in AAV2/2 injection eyes, whereas there were broad and uniform GFP signals in PMAAV-GST eyes.

FIG. 3. PMAAV-GST.CMV.eGFP targeted the retinal pigment epithelium (RPE) and Outer Nuclear Layer (ONL) layers, and some cells in the ganglion cell layer (GCL). AAV2/2 targeted the OPL primarily. CMV—Cytomegalovirus; eGFP—enhanced GFP.

FIG. 9. AAV2 Intravitreal injection.

DETAILED DESCRIPTION

Figure 4:
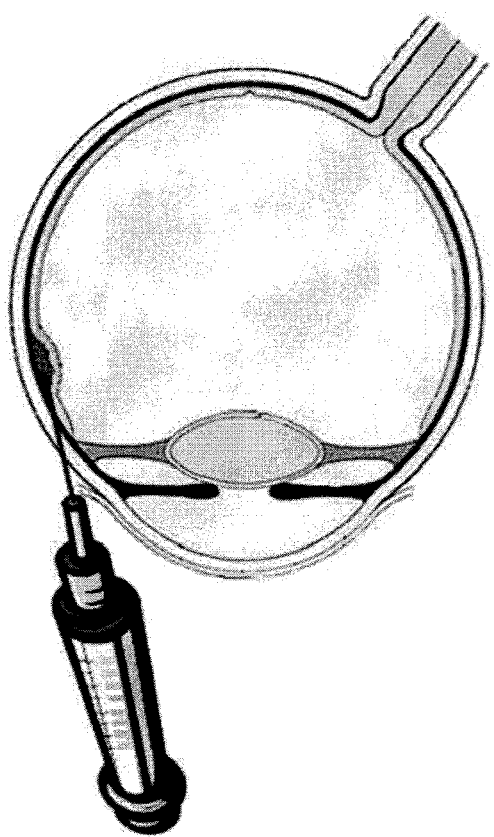
FIG. 4. Subretinal injection.
Figure 5:
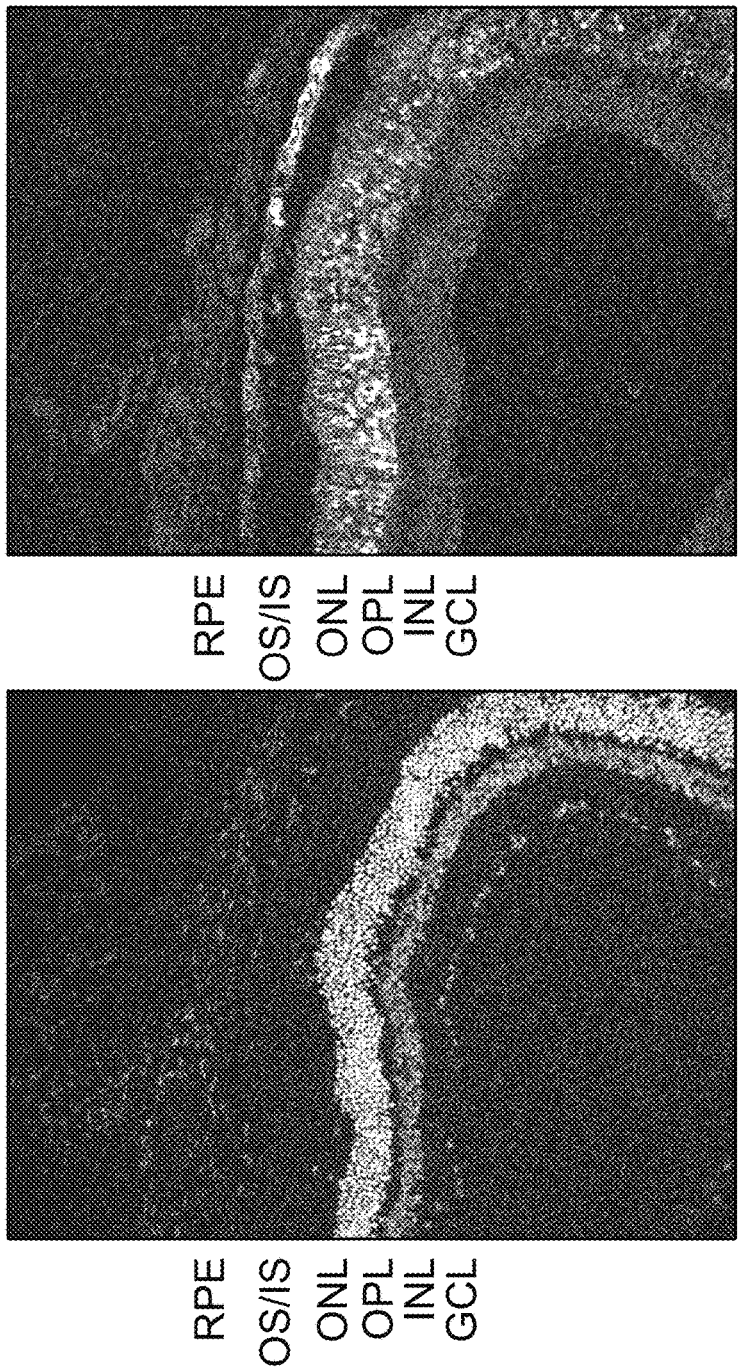
FIG. 5. Unmodified AAV2—subretinal injection.
Figure 6:
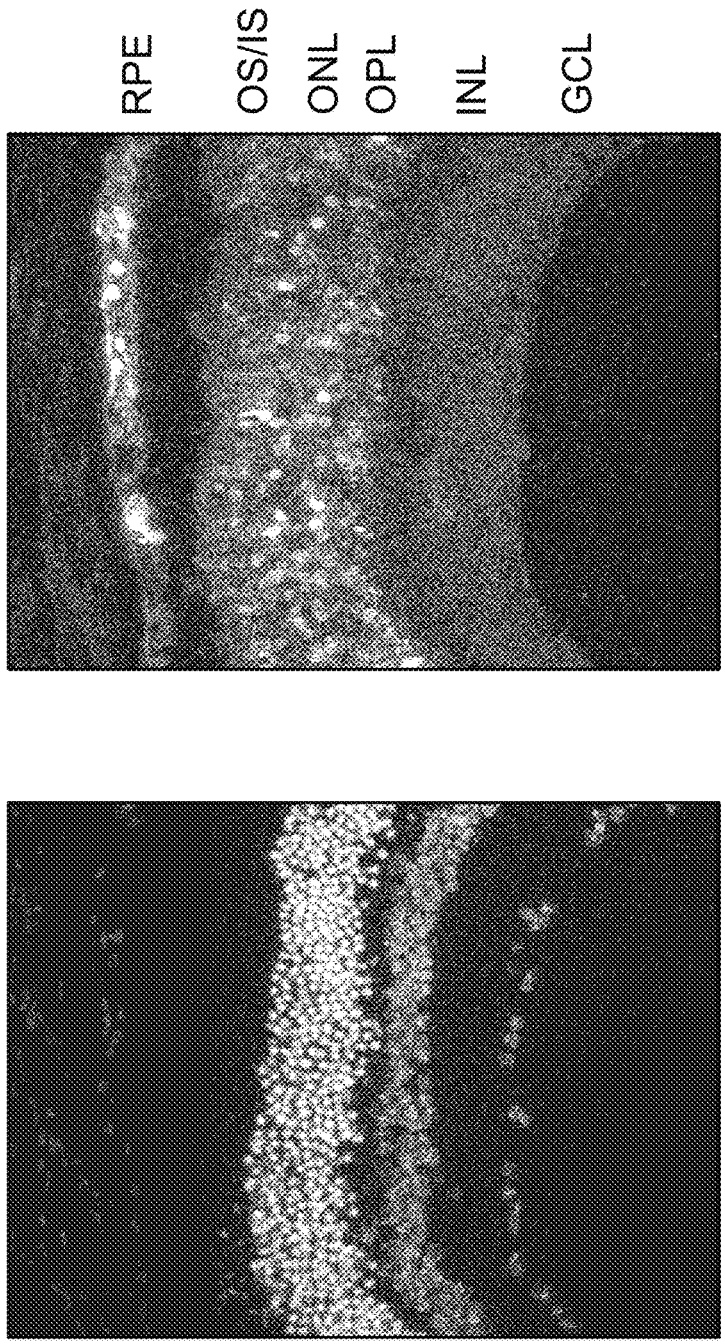
FIG. 6. Unmodified AAV2—subretinal injection.
Figure 7:
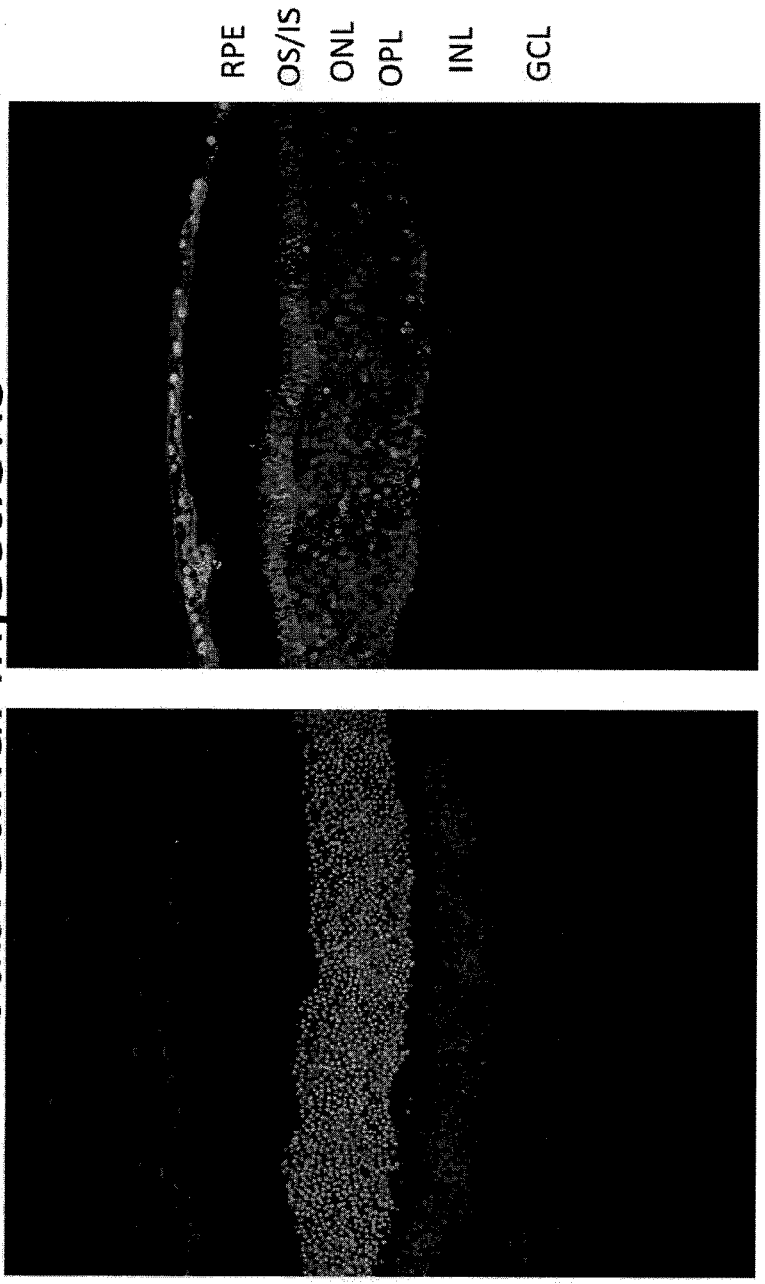
FIG. 7. 20× images PM modified AAV2—subretinal injection.
Figure 8:
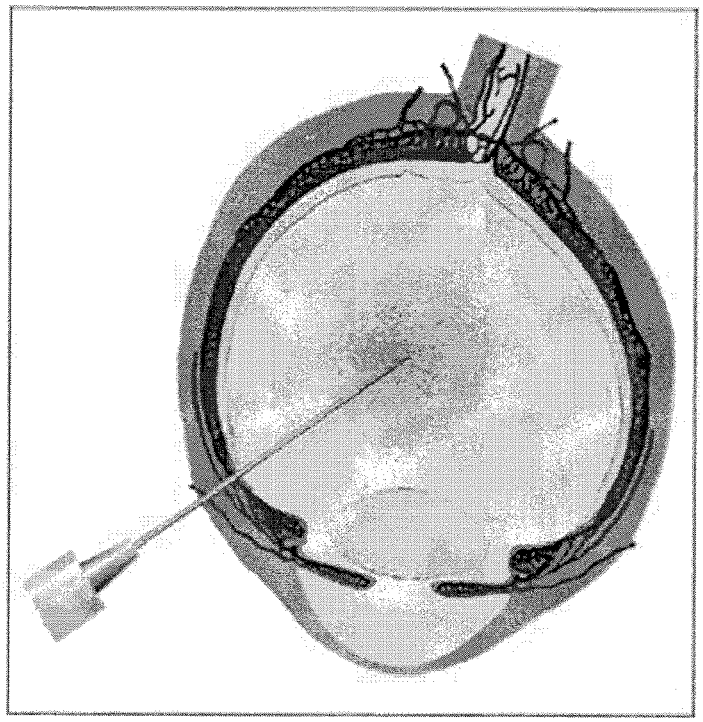
FIG. 8. Intravitreal injection.
Figure 10:
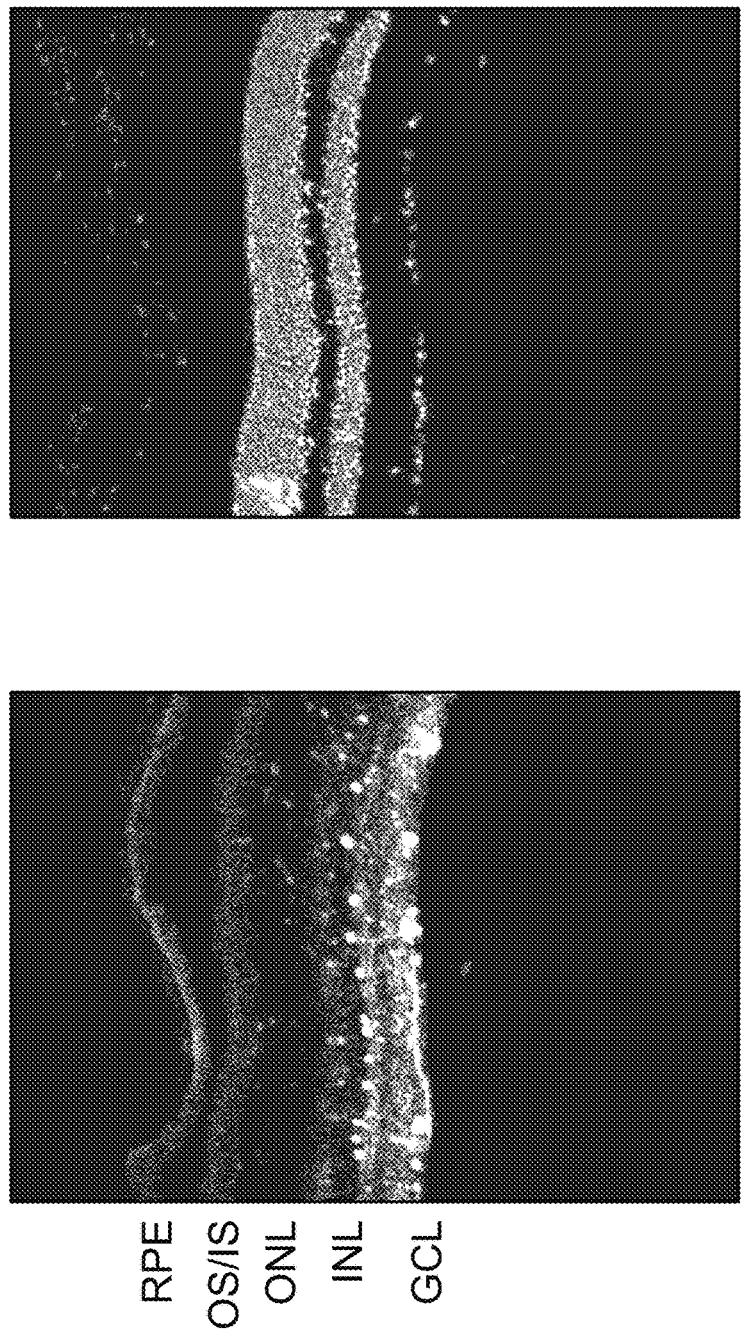
FIG. 10. AAV2 Intravitreal injection.
Figure 11:
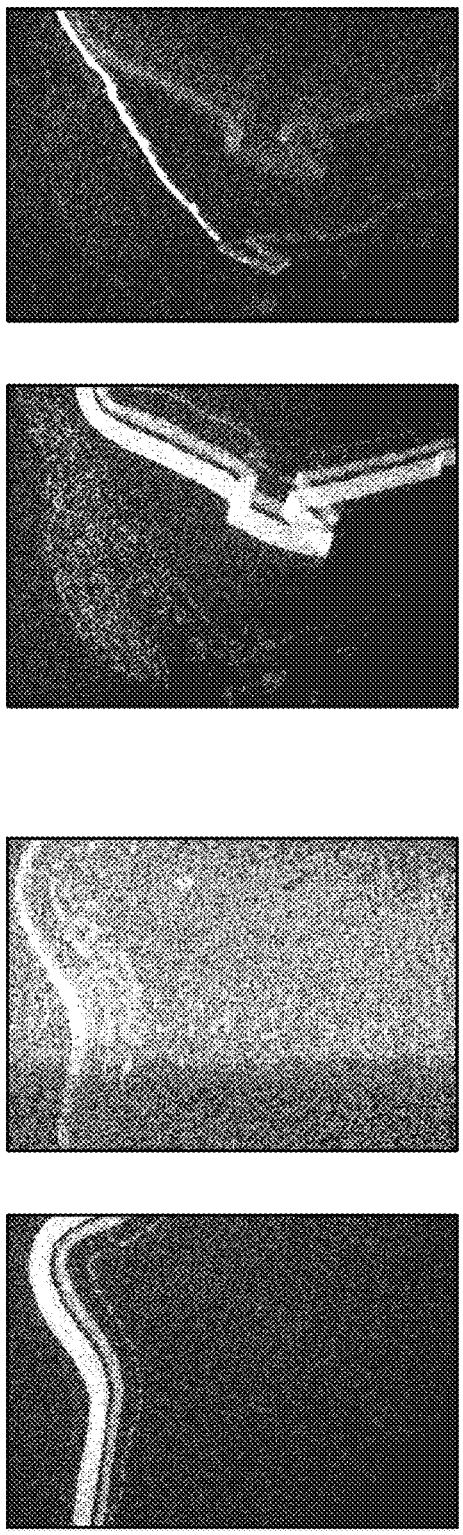
FIG. 11. AAV2 PM GST intravitreal injection.
Figure 12:
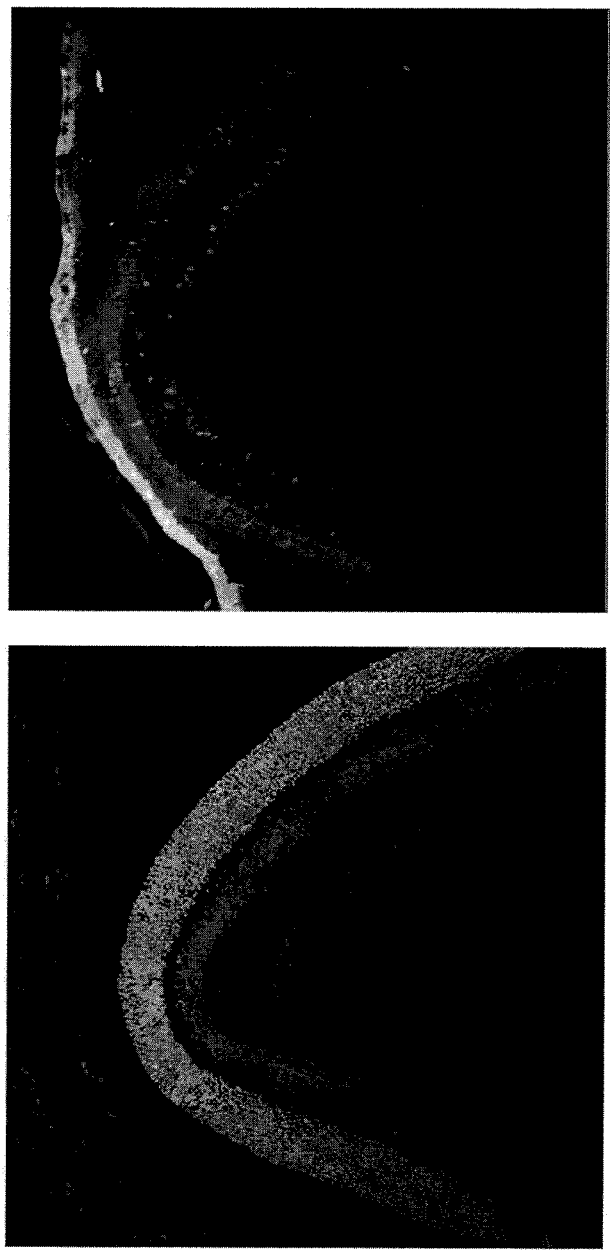
FIG. 12. AAV2 PM GST intravitreal injection.

Certain embodiments of the present disclosure provide a viral vector comprising a modified capsid, wherein the modified capsid comprises at least one amino acid sequence that targets the viral vector to ocular cells. In certain embodiments, the ocular cell is a retinal cell.

In certain embodiments, the viral vector is an adeno associated viral vector (AAV). In certain embodiments, the AAV is AAV2, although the tropism is modified so it would follow that such modifications would change the tropism of any AAV.

In certain embodiments, the targeting peptide comprises a sequence up to 10 amino acids in length having therein (or consisting of) of GSTPPPM (SEQ ID NO: 1) or amino acid sequence GETRAPL (SEQ ID NO: 4), as expressed in an amino to carboxy orientation or in a carboxy to amino orientation. It should be noted that the orientation of the sequence is not important. For example, the peptide may be oriented from the amino-terminal end to carboxy terminal end of the peptide to be GSTPPPM (SEQ ID NO:1) or may be from the amino-terminal end to carboxy-terminal end of the peptide to be MPPPTSG (SEQ ID NO:5).

In certain embodiments, the targeting peptide is inserted between the AAV2 capsid residues at positions P34-A35, T138-A139, A139-P140, G453-T454, N587-R588, and/or R588-Q589. An exemplary wildtype reference AAV2 capsid protein sequence is provided in SEQ ID NO:10.

In certain embodiments, the targeting peptide is inserted after the AAV9 capsid residues at positions D384, G385, I560, T561, N562, E563, E564, E565, N704, and/or Y705. An exemplary wildtype reference AAV9 capsid protein sequence is provided in SEQ ID NO:11.

In certain embodiments, the capsid protein comprises or consists of SEQ ID NO:8 or SEQ ID NO:9.

The present invention provides a viral vector comprising a nucleic acid encoding the capsid protein as described hereinabove. In certain embodiments, the viral vector further contains a nucleic acid sequence encoding a nucleic acid of interest. In certain embodiments, the nucleic acid of interest is a therapeutic agent. In certain embodiments, the therapeutic agent is an enzyme or an RNAi molecule (e.g., siRNA, shRNA or miRNA molecule). In certain embodiments, the therapeutic agent is Ataxin 7 mirRNA, RPE65, VEGF inhibitor or soluble VEGF receptor 1 (sFif1), REP1, L-opsin, Rho, PDE6β, ABCA4, LRAT, RDS/Peripherin, MERTK, IMPDH1, GUCY2D, RDS/Peripherin, AIPL1, ABCA4, RPGRIP1, IMPDH1, AIPL1, GUCY2D, LRAT, MERTK, RPGRIP1, RPE65, ABCA4, GNAT2, CNGB3, Rs1, OA1, (OCAI) tyrosinase, P21 WAF-1/Cipl, PDGF, Endostatin, Angiostatin, arylsulfatase B, or β-glucuronidase.

Certain embodiments of the present disclosure provide a nucleic acid sequence encoding a viral vector as described herein.

Certain embodiments of the present disclosure provide a nucleic acid sequence encoding a modified capsid as described herein. Certain embodiments of the present disclosure provide a nucleic acid sequence comprising or consisting of SEQ ID NO:2 (GGGTCGACGCCGCCTCCTATG). Certain embodiments of the present disclosure provide a modified capsid encoded by a nucleic acid sequence described herein.

Certain embodiments of the present disclosure provide a cell comprising a viral vector as described herein.

Certain embodiments of the present disclosure provide a cell transduced by a viral vector as described herein.

In certain embodiments, the cell is a mammalian cell. In certain embodiments, the cell is a human cell. In certain embodiments, the cell is a non-human cell. In certain embodiments, the cell is in vitro. In certain embodiments, the cell is in vivo. In certain embodiments, the cell is an ocular cell, such as a retinal cell.

Certain embodiments of the present disclosure provide a method of treating a disease in a mammal comprising administering a viral vector or the cell as described herein to the mammal. In certain embodiments, the targeting peptide targets a diseased ocular cell. In certain embodiments, the targeting peptide targets an ocular cell in a subject that has retinitis pigmentosa, maculopathies, Leber's congenital amaurosis, Leber's hereditary optic neuropathy, early onset severe retinal dystrophy, achromatopsia, retinoschisis, ocular albinism, oculocutaneous albinism, glaucoma, Stargardt disease, choroideremia, age-related macular degeneration, SCAT, color blindness, or lysosomal storage diseases that affect the cornea, such as MPS IV and MPS VII.

In certain embodiments, the subject has a lysosomal storage disease or disorder. In certain embodiments, the disease is a deficiency or defect in TPP1 (tripeptidyl peptidase I), CLN3 (Battenin), PPT1 (palmitoyl protein thioesterase I), CLN6 (neuronal ceroid lipofuscinosis protein 6) or CLN8 expression or activity. Diseases include neurodegenerative diseases such as neuronal ceroid lipofuscinosis (NCL), such as infantile NCL, late infantile NCL, juvenile NCL (Batten disease) and adult NCL.

In certain embodiments, the mammal is human.

Certain embodiments of the present disclosure provide a method to deliver an agent to the eye of a subject, comprising transducing ocular cells with a viral vector described herein so that the transduced ocular cells express the therapeutic agent and deliver the agent to the eye of the subject.

In certain embodiments, the viral vector transduces ocular cells.

In certain embodiments, the transduced ocular cells are within or comprise retina outer plexiform layer (OPL).

Certain embodiments of the present disclosure provide a viral vector or cell as described herein for use in medical treatment or diagnosis.

Certain embodiments of the present disclosure provide a use of a viral vector or cell as described herein to prepare a medicament useful for treating an ocular disease, e.g., a genetic eye disease, in a mammal.

Certain embodiments of the present disclosure provide a method for identifying peptides that target ocular tissue comprising using phage display biopanning so as to identify such peptides.

The vector may further comprise an enzyme, a secreted protein, a nuclear protein, or a cytoplasmic protein. As used herein, the term "secreted protein" includes any secreted protein, whether naturally secreted or modified to contain a signal sequence so that it can be secreted. For example, the secreted protein could be beta-glucuronidase.

Nucleic acid is "operably linked" when it is placed into a functional relationship with another nucleic acid sequence. Generally, "operably linked" means that the DNA sequences being linked are contiguous. However, enhancers do not have to be contiguous. Linking is accomplished by ligation at convenient restriction sites. If such sites do not exist, the synthetic oligonucleotide adaptors or linkers are used in accordance with conventional practice. Additionally, multiple copies of the nucleic acid encoding enzymes may be linked together in the expression vector. Such multiple nucleic acids may be separated by linkers.

The vector may be an adeno-associated virus (AAV) vector, an adenoviral vector, a retrovirus, or a lentivirus vector based on human immunodeficiency virus or feline immunodeficiency virus. Examples of such AAVs are found in Davidson et al., PNAS (2000) 97:3428-3432. The AAV and lentiviruses can confer lasting expression while the adenovirus can provide transient expression.

The present disclosure also provides a mammalian cell containing a vector described herein. The cell may be human, and may be from an eye. The cell type may be a stem or progenitor cell population.

The present disclosure provides a method of treating a disease such as a genetic eye disease or cancer in a mammal by administering a polynucleotide, polypeptide, expression vector, or cell described herein. The genetic eye disease or cancer may be retinitis pigmentosa, maculopathies, Leber's congenital amaurosis, Leber's hereditary optic neuropathy, early onset severe retinal dystrophy, achromatopsia, retinoschisis, ocular albinism, oculocutaneous albinism, glaucoma, Stargardt disease, choroideremia, age-related macular degeneration, SCAT, color blindness, and lysosomal storage diseases that affect the cornea, such as MPS IV and MPS VII.

The genetic disease may be a lysosomal storage disease or disorder. In certain embodiments, the disease is a deficiency or defect in TPP1 (tripeptidyl peptidase I), CLN3 (Battenin), PPT1 (palmitoyl protein thioesterase I), CLN6 (neuronal ceroid lipofuscinosis protein 6) or CLN8 expression or activity. The genetic disease may be a neurodegenerative disease, for example, a neuronal ceroid lipofuscinosis (NCL), such as infantile NCL, late infantile NCL, juvenile NCL (Batten disease) and adult NCL.

Certain aspects of the disclosure relate to polynucleotides, polypeptides, vectors, and genetically engineered cells (modified in vivo), and the use of them. In particular, the disclosure relates to a method for gene or protein therapy that is capable of local delivery of a therapeutically effective dose of the therapeutic agent.

According to one aspect, a cell expression system for expressing a therapeutic agent in a mammalian recipient is provided. The expression system (also referred to herein as a "genetically modified cell") comprises a cell and an expression vector for expressing the therapeutic agent. Expression vectors include, but are not limited to, viruses, plasmids, and other vehicles for delivering heterologous genetic material to cells. Accordingly, the term "expression vector" as used herein refers to a vehicle for delivering heterologous genetic material to a cell. In particular, the expression vector is a recombinant adenoviral, adeno-associated virus, or lentivirus or retrovirus vector.

The expression vector further includes a promoter for controlling transcription of the heterologous gene. The promoter may be an inducible promoter (described below). The expression system is suitable for administration to the mammalian recipient. The expression system may comprise a plurality of non-immortalized genetically modified cells, each cell containing at least one recombinant gene encoding at least one therapeutic agent.

The cell expression system can be formed in vivo. According to yet another aspect, a method for treating a mammalian recipient in vivo is provided. The method includes introducing an expression vector for expressing a heterologous gene product into a cell of the patient in situ, such as via intraocular administration. To form the expression system in vivo, an expression vector for expressing the therapeutic agent is introduced in vivo into the mammalian recipient.

According to yet another aspect, a method for treating a mammalian recipient in vivo is provided. The method includes introducing the target protein into the patient in vivo.

The expression vector for expressing the heterologous gene may include an inducible promoter for controlling transcription of the heterologous gene product. Accordingly, delivery of the therapeutic agent in situ is controlled by exposing the cell in situ to conditions, which induce transcription of the heterologous gene.

The mammalian recipient may have a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid or protein components.

According to one embodiment, the mammalian recipient has a genetic disease and the exogenous genetic material comprises a heterologous gene encoding a therapeutic agent for treating the disease. In yet another embodiment, the mammalian recipient has an acquired pathology and the exogenous genetic material comprises a heterologous gene encoding a therapeutic agent for treating the pathology. According to another embodiment, the patient has a cancer and the exogenous genetic material comprises a heterologous gene encoding an anti-neoplastic agent. In yet another embodiment the patient has an undesired medical condition and the exogenous genetic material comprises a heterologous gene encoding a therapeutic agent for treating the condition.

According to yet another embodiment, a pharmaceutical composition is disclosed. The pharmaceutical composition comprises a plurality of the above-described genetically modified cells or polypeptides and a pharmaceutically acceptable carrier. The pharmaceutical composition may be for treating a condition amenable to gene replacement therapy and the exogenous genetic material comprises a heterologous gene encoding a therapeutic agent for treating the condition. The pharmaceutical composition may contain an amount of genetically modified cells or polypeptides sufficient to deliver a therapeutically effective dose of the therapeutic agent to the patient. Exemplary conditions amenable to gene replacement therapy are described below.

According to another aspect, a method for forming the above-described pharmaceutical composition is provided. The method includes introducing an expression vector for expressing a heterologous gene product into a cell to form a genetically modified cell and placing the genetically modified cell in a pharmaceutically acceptable carrier.

These and other aspects, as well as various advantages and utilities will be more apparent with reference to the detailed description and to the accompanying Figures.

As used herein, the term "enzyme," a "secreted protein," a "nuclear protein," or a "cytoplasmic protein" include variants or biologically active or inactive fragments of these polypeptides. A "variant" of one of the polypeptides is a polypeptide that is not completely identical to a native protein. Such variant protein can be obtained by altering the amino acid sequence by insertion, deletion or substitution of one or more amino acid. The amino acid sequence of the protein is modified, for example by substitution, to create a polypeptide having substantially the same or improved qualities as compared to the native polypeptide. The substitution may be a conserved substitution. A "conserved substitution" is a substitution of an amino acid with another amino acid having a similar side chain. A conserved substitution would be a substitution with an amino acid that makes the smallest change possible in the charge of the amino acid or size of the side chain of the amino acid (alternatively, in the size, charge or kind of chemical group within the side chain) such that the overall peptide retains its spacial conformation but has altered biological activity. For example, common conserved changes might be Asp to Glu, Asn or Gln; His to Lys, Arg or Phe; Asn to Gln, Asp or Glu and Ser to Cys, Thr or Gly. Aline is commonly used to substitute for other amino acids. The 20 essential amino acids can be grouped as follows: alanine, valine, leucine, isoleucine, proline, phenylalanine, tryptophan and methionine having nonpolar side chains; glycine, serine, threonine, cystine, tyrosine, asparagine and glutamine having uncharged polar side chains; aspartate and glutamate having acidic side chains; and lysine, arginine, and histidine having basic side chains.

The amino acid changes are achieved by changing the codons of the corresponding nucleic acid sequence. It is known that such polypeptides can be obtained based on substituting certain amino acids for other amino acids in the polypeptide structure in order to modify or improve biological activity. For example, through substitution of alternative amino acids, small conformational changes may be conferred upon a polypeptide that results in increased activity. Alternatively, amino acid substitutions in certain polypeptides may be used to provide residues, which may then be linked to other molecules to provide peptide-molecule conjugates which retain sufficient properties of the starting polypeptide to be useful for other purposes.

One can use the hydropathic index of amino acids in conferring interactive biological function on a polypeptide, wherein it is found that certain amino acids may be substituted for other amino acids having similar hydropathic indices and still retain a similar biological activity. Alternatively, substitution of like amino acids may be made on the basis of hydrophilicity, particularly where the biological function desired in the polypeptide to be generated is intended for use in immunological embodiments. The greatest local average hydrophilicity of a "protein", as governed by the hydrophilicity of its adjacent amino acids, correlates with its immunogenicity. Accordingly, it is noted that substitutions can be made based on the hydrophilicity assigned to each amino acid.

In using either the hydrophilicity index or hydropathic index, which assigns values to each amino acid, it is preferred to conduct substitutions of amino acids where these values are ±2, with ±1 being particularly preferred, and those with in ±0.5 being the most preferred substitutions.

The variant protein has at least 50%, at least about 80%, or even at least about 90% but less than 100%, contiguous amino acid sequence homology or identity to the amino acid sequence of a corresponding native protein.

The amino acid sequence of the variant polypeptide corresponds essentially to the native polypeptide's amino acid sequence. As used herein "correspond essentially to" refers to a polypeptide sequence that will elicit a biological response substantially the same as the response generated by the native protein. Such a response may be at least 60% of the level generated by the native protein, and may even be at least 80% of the level generated by native protein.

A variant may include amino acid residues not present in the corresponding native protein or deletions relative to the corresponding native protein. A variant may also be a truncated "fragment" as compared to the corresponding native protein, i.e., only a portion of a full-length protein. Protein variants also include peptides having at least one D-amino acid.

The variant protein may be expressed from an isolated DNA sequence encoding the variant protein. "Recombinant" is defined as a peptide or nucleic acid produced by the processes of genetic engineering. It should be noted that it is well-known in the art that, due to the redundancy in the genetic code, individual nucleotides can be readily exchanged in a codon, and still result in an identical amino acid sequence. The terms "protein," "peptide" and "polypeptide" are used interchangeably herein.

The present disclosure provides methods of treating a disease in a mammal by administering an expression vector to a cell or patient. For the gene therapy methods, a person having ordinary skill in the art of molecular biology and gene therapy would be able to determine, without undue experimentation, the appropriate dosages and routes of administration of the expression vector used in the novel methods of the present disclosure.

According to one embodiment, the cells are transformed or otherwise genetically modified in vivo. The cells from the mammalian recipient are transformed (i.e., transduced or transfected) in vivo with a vector containing exogenous genetic material for expressing a heterologous (e.g., recombinant) gene encoding a therapeutic agent and the therapeutic agent is delivered in situ.

As used herein, "exogenous genetic material" refers to a nucleic acid or an oligonucleotide, either natural or synthetic, that is not naturally found in the cells; or if it is naturally found in the cells, it is not transcribed or expressed at biologically significant levels by the cells. Thus, "exogenous genetic material" includes, for example, a non-naturally occurring nucleic acid that can be transcribed into anti-sense RNA, as well as a "heterologous gene" (i.e., a gene encoding a protein which is not expressed or is expressed at biologically insignificant levels in a naturally-occurring cell of the same type).

In the certain embodiments, the mammalian recipient has a condition that is amenable to gene replacement therapy. As used herein, "gene replacement therapy" refers to administration to the recipient of exogenous genetic material encoding a therapeutic agent and subsequent expression of the administered genetic material in situ. Thus, the phrase "condition amenable to gene replacement therapy" embraces conditions such as genetic diseases (i.e., a disease condition that is attributable to one or more gene defects), acquired pathologies (i.e., a pathological condition which is not attributable to an inborn defect), cancers and prophylactic processes (i.e., prevention of a disease or of an undesired medical condition). Accordingly, as used herein, the term "therapeutic agent" refers to any agent or material, which has a beneficial effect on the mammalian recipient. Thus, "therapeutic agent" embraces both therapeutic and prophylactic molecules having nucleic acid (e.g., antisense RNA) and/or protein components.

A number of genetic eye diseases are known. Therapeutic agents effective against these diseases are also known, since it is the protein/enzyme known to be deficient in these disorders. In certain embodiments, the disease or condition is retinitis pigmentosa, maculopathies, Leber's congenital amaurosis, Leber's hereditary optic neuropathy, early onset severe retinal dystrophy, achromatopsia, retinoschisis, ocular albinism, oculocutaneous albinism, glaucoma, Stargardt disease, choroideremia, age-related macular degeneration, SCAT, color blindness, and lysosomal storage diseases that affect the cornea, such as MPS IV and MPS VII.

In certain embodiments, the disease or condition may be a lysosomal storage disease or disorder. In certain embodiments, the disease is a deficiency or defect in TPP1 (tripeptidyl peptidase I), CLN3 (Battenin), PPT1 (palmitoyl protein thioesterase I), CLN6 (neuronal ceroid lipofuscinosis protein 6) or CLN8 expression or activity. The disease may be a neurodegenerative disease such as neuronal ceroid lipofuscinosis (NCL), such as infantile NCL, late infantile NCL, juvenile NCL (Batten disease) and adult NCL.

As used herein, "acquired pathology" refers to a disease or syndrome manifested by an abnormal physiological, biochemical, cellular, structural, or molecular biological state. Exemplary acquired pathologies are provided in Table 2. Therapeutic agents effective against these diseases are also given.

refers to a non-naturally occurring DNA, which encodes a therapeutic agent. For example, many, if not all, of the agents disclosed in Tables 1-2 have known amino acid sequences, which are encoded by naturally occurring nucleic acids. However, due to the degeneracy of the genetic code, more than one nucleic acid can encode the same therapeutic agent. Accordingly, the instant disclosure embraces therapeutic agents encoded by naturally-occurring DNAs, as well as by non-naturally-occurring DNAs, which encode the same protein as, encoded by the naturally-occurring DNA.

The above-disclosed therapeutic agents and conditions amenable to gene replacement therapy are merely illustrative and are not intended to limit the scope of the instant disclosure. The selection of a suitable therapeutic agent for treating a known condition is deemed to be within the scope of one of ordinary skill of the art without undue experimentation.

Screening Methods

The present disclosure provides methods to screen for and identify amino acid sequences that target, e.g., specifically target, a specific area, such as the vasculature of the central nervous system. This method can be used to identify targeting sequences that are specific for specific disease states. In

TABLE 2

Potential Gene Therapies for Acquired Pathologies. Corresponding Proteins Encoded by the Genes are set forth in Table 1.

| Diseases | Target Gene for gene therapy |
| --- | --- |
| Retinitis Pigmentosa | Rho, PDE6β, ABCA4, RPE65, LRAT, RDS/Peripherin, MERTK, IMPDH1 |
| Maculopathies | GUCY2D, RDS/Peripherin, AIPL1, ABCA4, RPGRIP 1 |
| Leber's congenital amaurosis and early onset severe retinal dystrophy | IMPDH1, AIPL1, GUCY2D, LRAT, MERTK, RPGRIP1, RPE65 |
| Leber's hereditary optic neuropathy | Mitochondria Complex I genes, ND1, ND4, ND6, etc. |
| Stargardt disease, | ABCA4 |
| Achromatopsia | GNAT2, CNGB3 |
| X-linked retinoschisis | Rs1 |
| Ocular albinism | OA1 |
| Oculocutaneous albinism | (OCA1) tyrosinase |
| Glaucoma | P21 WAF-1/Cip1 |
| Choroideremia | REP-1 |
| Age related macular degeneration | PDGF, Endostatin Angiostatin, VEGF inhibitor |
| SCA 7 | Ataxin 7 mirRNA |
| Color blindness | Opsin |
| Lysosomal storage disease IV | arylsulfatase B |
| Lysosomal storage disease VII | β -glucuronidase |

Alternatively, the condition amenable to gene replacement therapy is a prophylactic process, i.e., a process for preventing disease or an undesired medical condition. Thus, the instant disclosure embraces a cell expression system for delivering a therapeutic agent that has a prophylactic function (i.e., a prophylactic agent) to the mammalian recipient.

In summary, the term "therapeutic agent" includes, but is not limited to, the agents listed in the Tables above, as well as their functional equivalents. As used herein, the term "functional equivalent" refers to a molecule (e.g., a peptide or protein) that has the same or an improved beneficial effect on the mammalian recipient as the therapeutic agent of which is it deemed a functional equivalent. As will be appreciated by one of ordinary skill in the art, a functionally equivalent proteins can be produced by recombinant techniques, e.g., by expressing a "functionally equivalent DNA." As used herein, the term "functionally equivalent DNA"

other words, targeting sequences may be identified and used in the treatment of specific diseases.

AAV Vectors

Adeno associated virus (AAV) is a small (20 nm), non-pathogenic virus that is useful in treating human diseases, such as Parkinson's disease and recessive genetic diseases. A construct is generated that surrounds a promoter linked to a target gene with AAV inverted terminal repeat (ITR) sequences.

In one embodiment, a viral vector of the disclosure is an AAV vector. An "AAV" vector refers to an adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many known serotypes of primate AAVs (e.g., AAV1, AAV2, AAV3, AAV4, AAV5, AAV6, AAV7, AAV8, AAV9, AAV 10, AAV-Rh74, and AAVRh10, and modified capsids of these serotypes). For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped rAAV are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

An "AAV virus" or "AAV viral particle" refers to a viral particle composed of at least one AAV capsid protein (preferably by all of the capsid proteins of a wild-type AAV) and an encapsidated polynucleotide. If the particle comprises heterologous polynucleotide (i.e., a polynucleotide other than a wild-type AAV genome such as a transgene to be delivered to a mammalian cell), it is typically referred to as "rAAV".

In one embodiment, the AAV expression vectors are constructed using known techniques to at least provide as operatively linked components in the direction of transcription, control elements including a transcriptional initiation region, the DNA of interest and a transcriptional termination region. The control elements are selected to be functional in a mammalian cell. The resulting construct which contains the operatively linked components is flanked (5' and 3') with functional AAV ITR sequences.

By "adeno-associated virus inverted terminal repeats" or "AAV ITRs" is meant the art recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See for example Kotin, R. M. (1994) Human Gene Therapy 5:793-801; Berns, K. I. "Parvoviridae and their Replication" in Fundamental Virology, 2nd Edition, (B. N. Fields and D. M. Knipe, eds.). As used herein, an "AAV ITR" need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV6, AAV7, AAV8, AAV9, AAV10, AAV-Rh74, and AAVRh10, and modified capsids of these serotypes. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell.

In one embodiment, AAV ITRs can be derived from any of several AAV serotypes, including without limitation, AAV1, AAV2, AAV3, AAV4, AAV5, AAV6, AAV7, AAV8, AAV9, AAV10, AAV-Rh74 (Rhesus macaque-derived AAV), and AAVRh10. Furthermore, 5' and 3' ITRs which flank a selected nucleotide sequence in an AAV expression vector need not necessarily be identical or derived from the same AAV serotype or isolate, so long as they function as intended, i.e., to allow for excision and rescue of the sequence of interest from a host cell genome or vector, and to allow integration of the DNA molecule into the recipient cell genome when AAV Rep gene products are present in the cell.

In one embodiment, AAV capsids can be derived from any of several AAV serotypes, including without limitation, AAV1, AAV2, AAV3, AAV4, AAV5, AAV6, AAV7, AAV8, AAV9, AAV10, AAV-Rh74 (Rhesus macaque-derived AAV), and AAVRh10, and the AAV ITRs are derived from AAV serotype 2. In certain embodiments, the AAV capsid is AAV2 capsid. Suitable DNA molecules for use in AAV vectors will be less than about 5 kilobases (kb), less than about 4.5 kb, less than about 4 kb, less than about 3.5 kb, less than about 3 kb, less than about 2.5 kb in size and are known in the art.

In some embodiments of the disclosure the DNA molecules for use in the AAV vectors will contain one or more copies of a single siRNA sequence. As used herein the term multiple copies of an siRNA sequences means at least 2 copies, at least 3 copies, at least 4 copies, at least 5 copies, at least 6 copies, at least 7 copies, at least 8 copies, at least 9 copies, and at least 10 copies. In some embodiments the DNA molecules for use in the AAV vectors will contain multiple siRNA sequences. As used herein the term multiple siRNA sequences means at least 2 siRNA sequences, at least 3 siRNA sequences, at least 4 siRNA sequences, at least 5 siRNA sequences, at least 6 siRNA sequences, at least 7 siRNA sequences, at least 8 siRNA sequences, at least 9 siRNA sequences, and at least 10 siRNA sequences. In some embodiments suitable DNA vectors of the disclosure will contain a sequence encoding the siRNA molecule of the disclosure and a stuffer fragment. Suitable stuffer fragments of the disclosure include sequences known in the art including without limitation sequences which do not encode an expressed protein molecule; sequences which encode a normal cellular protein which would not have deleterious effect on the cell types in which it was expressed; and sequences which would not themselves encode a functional siRNA duplex molecule.

In one embodiment, suitable DNA molecules for use in AAV vectors will be less than about 5 kilobases (kb) in size and will include, for example, a stuffer sequence and a sequence encoding a siRNA molecule of the disclosure. For example, in order to prevent any packaging of AAV genomic sequences containing the rep and cap genes, a plasmid containing the rep and cap DNA fragment may be modified by the inclusion of a stuffer fragment as is known in the art into the AAV genome which causes the DNA to exceed the length for optimal packaging. Thus, the helper fragment is not packaged into AAV virions. This is a safety feature, ensuring that only a recombinant AAV vector genome that does not exceed optimal packaging size is packaged into virions. An AAV helper fragment that incorporates a stuffer sequence can exceed the wild-type genome length of 4.6 kb, and lengths above 105% of the wild-type will generally not be packaged. The stuffer fragment can be derived from, for example, such non-viral sources as the Lac-Z or beta-galactosidase gene.

In one embodiment, the selected nucleotide sequence is operably linked to control elements that direct the transcription or expression thereof in the subject in vivo. Such control elements can comprise control sequences normally associated with the selected gene. Alternatively, heterologous control sequences can be employed. Useful heterologous control sequences generally include those derived from sequences encoding mammalian or viral genes. Examples include, but are not limited to, the Simian virus 40 (SV40) early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from nonviral genes, such as the murine metallothionein gene, will also find use herein. Such promoter sequences are commercially available from, e.g., Stratagene (San Diego, Calif.).

In one embodiment, both heterologous promoters and other control elements, such as retina-specific and inducible promoters, enhancers and the like, will be of particular use. Examples of heterologous promoters include the CMV promoter. Examples of retina-specific promoters include IRBP (interphotoreceptor retinoid-binding protein) promoter, hGRK1 (human rhodopsin kinase) promoter, IRBPe/GNAT2 (an enhancer element of interphotoreceptor retinoid-binding protein promoter) and a minimal sequence of the human transducin alpha-subunit promoter are examples of retina-specific promoter.

In one embodiment, the AAV expression vector which harbors the DNA molecule of interest bounded by AAV ITRs, can be constructed by directly inserting the selected sequence(s) into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art.

Alternatively, AAV ITRs can be excised from the viral genome or from an AAV vector containing the same and fused 5' and 3' of a selected nucleic acid construct that is present in another vector using standard ligation techniques. For example, ligations can be accomplished in 20 mM Tris-Cl pH 7.5, 10 mM MgCl2, 10 mM DTT, 33 gg/ml BSA, 10 mM-50 mM NaCl, and either 40 µM ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 30-100 µg/ml total DNA concentrations (5-100 nM total end concentration). AAV vectors which contain ITRs. In particular, several AAV vectors are described therein which are available from the American Type Culture Collection ("ATCC") under Accession Numbers 53222, 53223, 53224, 53225 and 53226.

Additionally, chimeric genes can be produced synthetically to include AAV ITR sequences arranged 5' and 3' of one or more selected nucleic acid sequences. The complete chimeric sequence is assembled from overlapping oligonucleotides prepared by standard methods.

In order to produce rAAV virions, an AAV expression vector is introduced into a suitable host cell using known techniques, such as by transfection. A number of transfection techniques are generally known in the art. See, e.g., Sambrook et al. (1989) Molecular Cloning, a laboratory manual, Cold Spring Harbor Laboratories, New York. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In one embodiment, suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used in the practice of the present disclosure. Particularly, the human cell line 293 is a human embryonic kidney cell line that has been transformed with adenovirus type-5 DNA fragments, and expresses the adenoviral E1a and E1b genes. The 293 cell line is readily transfected, and provides a particularly convenient platform in which to produce rAAV virions.

In one embodiment, host cells containing the above-described AAV expression vectors are rendered capable of providing AAV helper functions in order to replicate and encapsidate the nucleotide sequences flanked by the AAV ITRs to produce rAAV virions. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs (open reading frames), namely the rep and cap coding regions, or functional homologues thereof.

The Rep expression products have been shown to possess many functions, including, among others: recognition, binding and nicking of the AAV origin of DNA replication; DNA helicase activity; and modulation of transcription from AAV (or other heterologous) promoters. The Cap expression products supply necessary packaging functions. AAV helper functions are used herein to complement AAV functions in trans that are missing from AAV vectors.

In one embodiment, AAV helper functions are introduced into the host cell by transfecting the host cell with an AAV helper construct either prior to, or concurrently with, the transfection of the AAV expression vector. The term "AAV helper construct" refers generally to a nucleic acid molecule that includes nucleotide sequences providing AAV functions deleted from an AAV vector which is to be used to produce a transducing vector for delivery of a nucleotide sequence of interest. AAV helper constructs are commonly used to provide transient expression of AAV rep and/or cap genes to complement missing AAV functions that are necessary for lytic AAV replication; however, helper constructs lack AAV ITRs and can neither replicate nor package themselves. AAV helper constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors have been described which encode Rep and/or Cap expression products.

By "AAV rep coding region" is meant the art-recognized region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome. Suitable homologues of the AAV rep coding region include the human herpesvirus 6 (HHV-6) rep gene which is also known to mediate AAV-2 DNA replication.

By "AAV cap coding region" is meant the art-recognized region of the AAV genome which encodes the capsid proteins VP1, VP2, and VP3, or functional homologues thereof. These Cap expression products supply the packaging functions which are collectively required for packaging the viral genome. In certain embodiments, modifications, such as insertions are made in AAV2 capsid proteins at P34-A35, T138-A139, A139-P140, G453-T454, N587-R588, and/or R588-Q589. In certain embodiments, insertions are made at D384, G385, I560, T561, N562, E563, E564, E565, N704, and/or Y705 of AAV9.

In one embodiment, both AAV expression vectors and AAV helper constructs can be constructed to contain one or more optional selectable markers. Suitable markers include genes which confer antibiotic resistance or sensitivity to, impart color to, or change the antigenic characteristics of those cells which have been transfected with a nucleic acid construct containing the selectable marker when the cells are grown in an appropriate selective medium. Several selectable marker genes that are useful in the practice of the disclosure include the hygromycin B resistance gene (encoding Aminoglycoside phosphotranferase (APH)) that allows selection in mammalian cells by conferring resistance to G418 (available from Sigma, St. Louis, Mo.). Other suitable markers are known to those of skill in the art.

In one embodiment, the host cell (or packaging cell) is rendered capable of providing non AAV derived functions, or "accessory functions," in order to produce rAAV virions. Accessory functions are non AAV derived viral and/or cellular functions upon which AAV is dependent for its replication. Thus, accessory functions include at least those non AAV proteins and RNAs that are required in AAV replication, including those involved in activation of AAV gene transcription, stage specific AAV mRNA splicing, AAV DNA replication, synthesis of Cap expression products and AAV capsid assembly. Viral-based accessory functions can be derived from any of the known helper viruses.

In one embodiment, accessory functions can be introduced into and then expressed in host cells using methods known to those of skill in the art. Commonly, accessory functions are provided by infection of the host cells with an unrelated helper virus. A number of suitable helper viruses are known, including adenoviruses; herpesviruses such as herpes simplex virus types 1 and 2; and vaccinia viruses. Nonviral accessory functions will also find use herein, such as those provided by cell synchronization using any of various known agents.

In one embodiment, accessory functions are provided using an accessory function vector. Accessory function vectors include nucleotide sequences that provide one or more accessory functions. An accessory function vector is capable of being introduced into a suitable host cell in order to support efficient AAV virion production in the host cell. Accessory function vectors can be in the form of a plasmid, phage, transposon or cosmid. Accessory vectors can also be in the form of one or more linearized DNA or RNA fragments which, when associated with the appropriate control elements and enzymes, can be transcribed or expressed in a host cell to provide accessory functions.

In one embodiment, nucleic acid sequences providing the accessory functions can be obtained from natural sources, such as from the genome of an adenovirus particle, or constructed using recombinant or synthetic methods known in the art. In this regard, adenovirus-derived accessory functions have been widely studied, and a number of adenovirus genes involved in accessory functions have been identified and partially characterized. Specifically, early adenoviral gene regions E1a, E2a, E4, VAI RNA and, possibly, E1b are thought to participate in the accessory process. Herpesvirus-derived accessory functions have been described. Vaccinia virus-derived accessory functions have also been described.

In one embodiment, as a consequence of the infection of the host cell with a helper virus, or transfection of the host cell with an accessory function vector, accessory functions are expressed which transactivate the AAV helper construct to produce AAV Rep and/or Cap proteins. The Rep expression products excise the recombinant DNA (including the DNA of interest) from the AAV expression vector. The Rep proteins also serve to duplicate the AAV genome. The expressed Cap proteins assemble into capsids, and the recombinant AAV genome is packaged into the capsids. Thus, productive AAV replication ensues, and the DNA is packaged into rAAV virions.

In one embodiment, following recombinant AAV replication, rAAV virions can be purified from the host cell using a variety of conventional purification methods, such as CsCl gradients. Further, if infection is employed to express the accessory functions, residual helper virus can be inactivated, using known methods. For example, adenovirus can be inactivated by heating to temperatures of approximately 60° C. for, e.g., 20 minutes or more. This treatment effectively inactivates only the helper virus since AAV is extremely heat stable while the helper adenovirus is heat labile. The resulting rAAV virions are then ready for use for DNA delivery to the eye of the subject.

Methods of delivery of viral vectors include, but are not limited to, intra-ocular, sub retinal, and intra-vitreal routes. Generally, rAAV virions may be introduced into cells of the eye using either in vivo or in vitro transduction techniques. If transduced in vitro, the desired recipient cell will be removed from the subject, transduced with rAAV virions and reintroduced into the subject. Alternatively, syngeneic or xenogeneic cells can be used where those cells will not generate an inappropriate immune response in the subject.

Suitable methods for the delivery and introduction of transduced cells into a subject have been described. For example, cells can be transduced in vitro by combining recombinant AAV virions with ocular cells e.g., in appropriate media, and screening for those cells harboring the DNA of interest can be screened using conventional techniques such as Southern blots and/or PCR, or by using selectable markers. Transduced cells can then be formulated into pharmaceutical compositions, described more fully below, and the composition introduced into the subject by various techniques, such as by grafting, intramuscular, intravenous, subcutaneous and intraperitoneal injection.

In one embodiment, for in vivo delivery, the rAAV virions are formulated into pharmaceutical compositions and will generally be administered intra-ocularly, e.g., by injection sub-retinally.

In one embodiment, pharmaceutical compositions will comprise sufficient genetic material to produce a therapeutically effective amount of the nucleic acid of interest, i.e., an amount sufficient to reduce or ameliorate symptoms of the disease state in question or an amount sufficient to confer the desired benefit. The pharmaceutical compositions will also contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like, may be present in such vehicles. A thorough discussion of pharmaceutically acceptable excipients is available in Remington's Pharmaceutical Sciences (Mack Pub. Co., N.J. 1991).

As is apparent to those skilled in the art in view of the teachings of this specification, an effective amount of viral vector which must be added can be empirically determined. Administration can be effected in one dose, continuously or intermittently throughout the course of treatment. Methods of determining the most effective means and dosages of administration are well known to those of skill in the art and will vary with the viral vector, the composition of the therapy, the target cells, and the subject being treated. Single and multiple administrations can be carried out with the dose level and pattern being selected by the treating physician.

It should be understood that more than one transgene could be expressed by the delivered viral vector. Alternatively, separate vectors, each expressing one or more different transgenes, can also be delivered to the eye as described herein. Furthermore, it is also intended that the viral vectors delivered by the methods of the present disclosure be combined with other suitable compositions and therapies.

Methods for Introducing Genetic Material into Cells

The exogenous genetic material (e.g., a cDNA encoding one or more therapeutic proteins) is introduced into the cell ex vivo or in vivo by genetic transfer methods, such as transfection or transduction, to provide a genetically modified cell. Various expression vectors (i.e., vehicles for facilitating delivery of exogenous genetic material into a target cell) are known to one of ordinary skill in the art.

As used herein, "transfection of cells" refers to the acquisition by a cell of new genetic material by incorporation of added DNA. Thus, transfection refers to the insertion of nucleic acid into a cell using physical or chemical methods. Several transfection techniques are known to those of ordinary skill in the art including: calcium phosphate DNA co-precipitation; DEAE-dextran; electroporation; cationic liposome-mediated transfection; and tungsten particle-facilitated microparticle bombardment. Strontium phosphate DNA co-precipitation is another possible transfection method.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous genetic material contained within the retrovirus is incorporated into the genome of the transduced cell. A cell that has been transduced with a chimeric DNA virus (e.g., an adenovirus carrying a cDNA encoding a therapeutic agent), will not have the exogenous genetic material incorporated into its genome but will be capable of expressing the exogenous genetic material that is retained extrachromosomally within the cell.

Typically, the exogenous genetic material includes the heterologous gene (usually in the form of a cDNA comprising the exons coding for the therapeutic protein) together with a promoter to control transcription of the new gene. The promoter characteristically has a specific nucleotide sequence necessary to initiate transcription. Optionally, the exogenous genetic material further includes additional sequences (i.e., enhancers) required to obtain the desired gene transcription activity. For the purpose of this discussion an "enhancer" is simply any non-translated DNA sequence which works contiguous with the coding sequence (in cis) to change the basal transcription level dictated by the promoter. The exogenous genetic material may introduced into the cell genome immediately downstream from the promoter so that the promoter and coding sequence are operatively linked so as to permit transcription of the coding sequence. A retroviral expression vector may include an exogenous promoter element to control transcription of the inserted exogenous gene. Such exogenous promoters include both constitutive and inducible promoters.

Naturally-occurring constitutive promoters control the expression of essential cell functions. As a result, a gene under the control of a constitutive promoter is expressed under all conditions of cell growth. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eucaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Genes that are under the control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting the appropriate promoter (constitutive versus inducible; strong versus weak), it is possible to control both the existence and level of expression of a therapeutic agent in the genetically modified cell. If the gene encoding the therapeutic agent is under the control of an inducible promoter, delivery of the therapeutic agent in situ is triggered by exposing the genetically modified cell in situ to conditions for permitting transcription of the therapeutic agent, e.g., by intraperitoneal injection of specific inducers of the inducible promoters which control transcription of the agent. For example, in situ expression by genetically modified cells of a therapeutic agent encoded by a gene under the control of the metallothionein promoter, is enhanced by contacting the genetically modified cells with a solution containing the appropriate (i.e., inducing) metal ions in situ.

Accordingly, the amount of therapeutic agent that is delivered in situ is regulated by controlling such factors as: (1) the nature of the promoter used to direct transcription of the inserted gene, (i.e., whether the promoter is constitutive or inducible, strong or weak); (2) the number of copies of the exogenous gene that are inserted into the cell; (3) the number of transduced/transfected cells that are administered (e.g., implanted) to the patient; (4) the size of the implant (e.g., graft or encapsulated expression system); (5) the number of implants; (6) the length of time the transduced/transfected cells or implants are left in place; and (7) the production rate of the therapeutic agent by the genetically modified cell. Selection and optimization of these factors for delivery of a therapeutically effective dose of a particular therapeutic agent is deemed to be within the scope of one of ordinary skill in the art without undue experimentation, taking into account the above-disclosed factors and the clinical profile of the patient.

In addition to at least one promoter and at least one heterologous nucleic acid encoding the therapeutic agent, the expression vector may include a selection gene, for example, a neomycin resistance gene, for facilitating selection of cells that have been transfected or transduced with the expression vector. Alternatively, the cells are transfected with two or more expression vectors, at least one vector containing the gene(s) encoding the therapeutic agent(s), the other vector containing a selection gene. The selection of a suitable promoter, enhancer, selection gene and/or signal sequence (described below) is deemed to be within the scope of one of ordinary skill in the art without undue experimentation.

The therapeutic agent can be targeted for delivery to an extracellular, intracellular or membrane location. If it is desirable for the gene product to be secreted from the cells, the expression vector is designed to include an appropriate secretion "signal" sequence for secreting the therapeutic gene product from the cell to the extracellular milieu. If it is desirable for the gene product to be retained within the cell, this secretion signal sequence is omitted. In a similar manner, the expression vector can be constructed to include "retention" signal sequences for anchoring the therapeutic agent within the cell plasma membrane. For example, all membrane proteins have hydrophobic transmembrane regions, which stop translocation of the protein in the membrane and do not allow the protein to be secreted. The construction of an expression vector including signal sequences for targeting a gene product to a particular location is deemed to be within the scope of one of ordinary skill in the art without the need for undue experimentation.

The following discussion is directed to various utilities of the instant disclosure. For example, the instant disclosure has utility as an expression system suitable for detoxifying intra—and/or extracellular toxins in situ. By attaching or omitting the appropriate signal sequence to a gene encoding a therapeutic agent capable of detoxifying a toxin, the therapeutic agent can be targeted for delivery to the extracellular milieu, to the cell plasma membrane or to an intracellular location. In one embodiment, the exogenous genetic material containing a gene encoding an intracellular detoxifying therapeutic agent, further includes sequences encoding surface receptors for facilitating transport of extracellular toxins into the cell where they can be detoxified intracellularly by the therapeutic agent. Alternatively, the cells can be genetically modified to express the detoxifying therapeutic agent anchored within the cell plasma membrane such that the active portion extends into the extracellular milieu. The active portion of the membrane-bound therapeutic agent detoxifies toxins, which are present in the extracellular milieu.

In addition to the above-described therapeutic agents, some of which are targeted for intracellular retention, the instant disclosure also embraces agents intended for delivery to the extracellular milieu and/or agents intended to be anchored in the cell plasma membrane.

The selection and optimization of a particular expression vector for expressing a specific gene product in an isolated cell is accomplished by obtaining the gene, potentially with one or more appropriate control regions (e.g., promoter, insertion sequence); preparing a vector construct comprising the vector into which is inserted the gene; transfecting or transducing cultured cells in vitro with the vector construct; and determining whether the gene product is present in the cultured cells. In certain embodiments, a virus from the adeno-associated virus family is used. In certain embodiments, an expression vector for gene therapy based on AAV2, AAV4 and/or AAV5 is used.

Thus, as will be apparent to one of ordinary skill in the art, a variety of suitable viral expression vectors are available for transferring exogenous genetic material into cells. The selection of an appropriate expression vector to express a therapeutic agent for a particular condition amenable to gene replacement therapy and the optimization of the conditions for insertion of the selected expression vector into the cell, are within the scope of one of ordinary skill in the art without the need for undue experimentation.

In an alternative embodiment, the expression vector is in the form of a plasmid, which is transferred into the target cells by one of a variety of methods: physical (e.g., microinjection, electroporation, scrape loading, microparticle bombardment) or by cellular uptake as a chemical complex (e.g., calcium or strontium co-precipitation, complexation with lipid, complexation with ligand). Several commercial products are available for cationic liposome complexation including Lipofectin™ (Gibco-BRL, Gaithersburg, Md.) and Transfectam™ (ProMega, Madison, Wis.). However, the efficiency of transfection by these methods is highly dependent on the nature of the target cell and accordingly, the conditions for optimal transfection of nucleic acids into cells using the above-mentioned procedures must be optimized. Such optimization is within the scope of one of ordinary skill in the art without the need for undue experimentation.

The instant disclosure also provides various methods for making and using the above-described genetically-modified cells. As used herein, the term "isolated" means a cell or a plurality of cells that have been removed from their naturally-occurring in vivo location. Methods for removing cells from a patient, as well as methods for maintaining the isolated cells in culture are known to those of ordinary skill in the art.

The instant disclosure also provides methods for genetically modifying cells of a mammalian recipient in vivo. According to one embodiment, the method comprises introducing an expression vector for expressing a heterologous gene product into cells of the mammalian recipient in situ by, for example, injecting the vector into the recipient.

In one embodiment, the preparation of genetically modified cells contains an amount of cells sufficient to deliver a therapeutically effective dose of the therapeutic agent to the recipient in situ. The determination of a therapeutically effective dose of a specific therapeutic agent for a known condition is within the scope of one of ordinary skill in the art without the need for undue experimentation. Thus, in determining the effective dose, one of ordinary skill would consider the condition of the patient, the severity of the condition, as well as the results of clinical studies of the specific therapeutic agent being administered.

If the genetically modified cells are not already present in a pharmaceutically acceptable carrier they are placed in such a carrier prior to administration to the recipient. Such pharmaceutically acceptable carriers include, for example, isotonic saline and other buffers as appropriate to the patient and therapy.

More than one recombinant gene can be introduced into each genetically modified cell on the same or different vectors, thereby allowing the expression of multiple therapeutic agents by a single cell.

EXAMPLE 1

Preparation of Modified AAVs that Target Ocular Cells

The present inventors designed AAVs that are modified to target ocular cells after local delivery. To generate an adeno-associated virus (AAV) that targets the ocular cells, the inventors first used in vivo phage display panning to identify peptide motifs that bind preferentially to ocular cells. A phage-display library was injected into the eyes of mice, and eye cells were subsequently isolated along with the bound phage. The isolated phage was then amplified and reinjected, and after five rounds of such in vivo panning, DNA sequencing of the recovered phage revealed an enrichment of distinct peptide motifs from the initial phage library.

In the mice, the peptide motifs GSTPPPM (SEQ ID NO: 1) and GETRAPL (SEQ ID NO: 4) were identified. To confirm the affinity of these phage for the ocular cells, each phage was individually re-injected intravenously into mice, and visualized. Consistent with the panning results, each of the selected phage accumulated in eye beyond the background levels observed for controls.

Peptide-modified AAVs were generated by inserting the peptides identified from phage display panning into the AAV2 capsid. Peptides were inserted between positions 587 and 588 of the VP3 capsid protein to yield clones. AAV-WT (Wild Type, no insert) served as a control virus. The 587/588 site is located in a domain of the VP3 capsid protein involved in the binding of AAV2 with its major receptor, heparin sulfate proteoglycan (HSPG), and insertion of peptides in this site can alter the tropism of AAV without compromising virus viability. The modified capsid proteins packaged AAV vector genomes with genomic titers comparable to those of wildtype virus.

```
Sequence of AAV2 wild-type capsid
         587 588
5'-AGA GGC AAC AGA CAA GCA-3'    (SEQ ID NO: 6)
   R   G   N   R   Q   A         (SEQ ID NO: 7)
```

The sequence of AAV2 wild type capsid is depicted below in SEQ ID NO:8.

```
                                              (SEQ ID NO: 8)
MAADGYLPDWLEDTLSEGIRQWWKLKPGPPPPKPAERHKDDSRGLV

LPGYKYLGPFNGLDKGEPVNEADAAALEHDKAYDRQLDSGDNPYLK

YNHADAEFQERLKEDTSFGGNLGRAVFQAKKRVLEPLGLVEEPVKT
```

```
APGKKRPVEHSPVEPDSSSGTGKAGQQPARKRLNFGQTGDADSVPD

PQPLGQPPAAPSGLGTNTMATGSGAPMADNNEGADGVGNSSGNWHC

DSTWMGDRVITTSTRTWALPTYNNHLYKQISSQSGASNDNHYFGYS

TPWGYFDFNRFHCHFSPRDWQRLINNNWGFRPKRLNFKLFNIQVKE

VTQNDGTTTIANNLTSTVQVFTDSEYQLPYVLGSAHQGCLPPFPAD

VFMVPQYGYLTLNNGSQAVGRSSFYCLEYFPSQMLRTGNNFTFSYT

FEDVPFHSSYAHSQSLDRLMNPLIDQYLYYLSRTNTPSGTTTQSRL

QFSQAGASDIRDQSRNWLPGPCYRQQRVSKTSADNNNSEYSWTGAT

KYHLNGRDSLVNPGPAMASHKDDEEKFFPQSGVLIFGKQGSEKTNV

DIEKVMITDEEEIRTTNPVATEQYGSVSTNLQRGNRQAATADVNTQ

GVLPGMVWQDRDVYLQGPIWAKIPHTDGHFHPSPLMGGFGLKHPPP

QILIKNTPVPANPSTTFSAAKFASFITQYSTGQVSVEIEWELQKEN

SKRWNPEIQYTSNYNKSVNVDFTVDTNGVYSEPRPIGTRYLTRNL*
```

In the example below, the sequence of AAV2 wild type capsid with inserted motif (SEQ ID NO:1) that targets ocular cells is italicized, and the underlined amino acids are spacers.

```
                                              (SEQ ID NO: 9)
MAADGYLPDWLEDTLSEGIRQWWKLKPGPPPPKPAERHKDDSRGLV

LPGYKYLGPFNGLDKGEPVNEADAAALEHDKAYDRQLDSGDNPYLK

YNHADAEFQERLKEDTSFGGNLGRAVFQAKKRVLEPLGLVEEPVKT

APGKKRPVEHSPVEPDSSSGTGKAGQQPARKRLNFGQTGDADSVPD

PQPLGQPPAAPSGLGTNTMATGSGAPMADNNEGADGVGNSSGNWHC

DSTWMGDRVITTSTRTWALPTYNNHLYKQISSQSGASNDNHYFGYS

TPWGYFDFNRFHCHFSPRDWQRLINNNWGFRPKRLNFKLFNIQVKE

VTQNDGTTTIANNLTSTVQVFTDSEYQLPYVLGSAHQGCLPPFPAD

VFMVPQYGYLTLNNGSQAVGRSSFYCLEYFPSQMLRTGNNFTFSYT

FEDVPFHSSYAHSQSLDRLMNPLIDQYLYYLSRTNTPSGTTTQSRL

QFSQAGASDIRDQSRNWLPGPCYRQQRVSKTSADNNNSEYSWTGAT

KYHLNGRDSLVNPGPAMASHKDDEEKFFPQSGVLIFGKQGSEKTNV

DIEKVMITDEEEIRTTNPVATEQYGSVSTNLQRGN<u>AAA</u>*GSTPPPM*<u>A</u>

<u>AR</u>QAATADVNTQGVLPGMVWQDRDVYLQGPIWAKIPHTDGHFHPSP

LMGGFGLKHPPPQILIKNTPVPANPSTTFSAAKFASFITQYSTGQV

SVEIEWELQKENSKRWNPEIQYTSNYNKSVNVDFTVDTNGVYSEPR

PIGTRYLTRNL*
```

The sequence of AAV2 wild type capsid with SEQ ID NO:4 inserted motif is depicted below in SEQ ID NO:10. The amino acid motif that targets ocular cells is italicized, and the underlined amino acids are spacers.

```
                                             (SEQ ID NO: 10)
MAADGYLPDWLEDTLSEGIRQWWKLKPGPPPPKPAERHKDDSRGLV

LPGYKYLGPFNGLDKGEPVNEADAAALEHDKAYDRQLDSGDNPYLK
```

-continued
```
YNHADAEFQERLKEDTSFGGNLGRAVFQAKKRVLEPLGLVEEPVKT

APGKKRPVEHSPVEPDSSSGTGKAGQQPARKRLNFGQTGDADSVPD

PQPLGQPPAAPSGLGTNTMATGSGAPMADNNEGADGVGNSSGNWHC

DSTWMGDRVITTSTRTWALPTYNNHLYKQISSQSGASNDNHYFGYS

TPWGYFDFNRFHCHFSPRDWQRLINNNWGFRPKRLNFKLFNIQVKE

VTQNDGTTTIANNLTSTVQVFTDSEYQLPYVLGSAHQGCLPPFPAD

VFMVPQYGYLTLNNGSQAVGRSSFYCLEYFPSQMLRTGNNFTFSYT

FEDVPFHSSYAHSQSLDRLMNPLIDQYLYYLSRTNTPSGTTTQSRL

QFSQAGASDIRDQSRNWLPGPCYRQQRVSKTSADNNNSEYSWTGAT

KYHLNGRDSLVNPGPAMASHKDDEEKFFPQSGVLIFGKQGSEKTNV

DIEKVMITDEEEIRTTNPVATEQYGSVSTNLQRGNAAAGETRAPLA

ARQAATADVNTQGVLPGMVWQDRDVYLQGPIWAKIPHTDGHFHPSP

LMGGFGLKHPPPQILIKNTPVPANPSTTFSAAKFASFITQYSTGQV

SVEIEWELQKENSKRWNPEIQYTSNYNKSVNVDFTVDTNGVYSEPR

PIGTRYLTRNL*
```

The sequence of AAV9 wild type capsid is depicted below in SEQ ID NO:11.

```
                                        (SEQ ID NO: 11)
MAADGYLPDWLEDNLSEGIREWWALKPGAPQPKANQQHQDNARGLV

LPGYKYLGPGNGLDKGEPVNAADAAALEHDKAYDQQLKAGDNPYLK

YNHADAEFQERLKEDTSFGGNLGRAVFQAKKRLLEPLGLVEEAAKT

APGKKRPVEQSPQEPDSSAGIGKSGAQPAKKRLNFGQTGDTESVPD

PQPIGEPPAAPSGVGSLTMASGGGAPVADNNEGADGVGSSSGNWHC

DSQWLGDRVITTSTRTWALPTYNNHLYKQISNSTSGGSSNDNAYFG

YSTPWGYFDFNRFHCHFSPRDWQRLINNNWGFRPKRLNFKLFNIQV

KEVTDNNGVKTIANNLTSTVQVFTDSDYQLPYVLGSAHEGCLPPFP

ADVFMIPQYGYLTLNDGSQAVGRSSFYCLEYFPSQMLRTGNNFQFS

YEFENVPFHSSYAHSQSLDRLMNPLIDQYLYYLSKTINGSGQNQQT

LKFSVAGPSNMAVQGRNYIPGPSYRQQRVSTTVTQNNNSEFAWPGA

SSWALNGRNSLMNPGPAMASHKEGEDRFFPLSGSLIFGKQGTGRDN

VDADKVMITNEEEIKTTNPVATESYGQVATNHQSAQAQAQTGWVQN

QGILPGMVWQDRDVYLQGPIWAKIPHTDGNFHPSPLMGGFGMKHPP

PQILIKNTPVPADPPTAFNKDKLNSFITQYSTGQVSVEIEWELQKE

NSKRWNPEIQYTSNYYKSNNVEFAVNTEGVYSEPRPIGTRYLTRNL*
```

Materials and Methods:

In Vivo Biopanning:

1 μl of Ph.D.™ 7 phage library (titer 2.0×10[13] pfu/ml from neb) was injected into the subretinal space of mice eyes. After 30 minutes, the retina and RPE from injected eye were separated, washed with 5 ml cold PBS 3-5 times. The retina and RPE were homogenized in 500 ul PBS. The recovered phage were titered, amplified, purified, and re-injected into additional eyes for the next round of in vivo panning. The whole procedure was repeated for four rounds. After this, 50 random selected clones were sequenced to determine enriched motifs.

Construction of Peptide Modified AAV2 Capsids:

The plasmid for cloning of modified capsids was developed from pXX2, containing the wild-type AAV2 Rep and Cap. A plasmid with a DNA fragment encoding amino acids AAAstopA and the restriction sites NotI and AscI inserted between AAV2 Cap amino acid position 587 and 588 was constructed as the backbone plasmid. dsDNA inserts encoding selected peptides were cloned into NotI and AscI site as peptide modified pXX2.

AAV2 Production and Titer:

Plates of 293T cells were cotransfected with three plasmids: pXX2 or peptide modified pXX2, which supplied the Rep and Cap proteins of AAV2; pHelper, which contained the adenovirus helper functions; and a vector plasmid, which contained the AAV2 ITRs and the transgene of interest. Twenty 150 mm-diameter plates were cotransfected 90 μg DNA of plasmids pXX2, pHelper, and vector at a molar ratio of 1:1:1. After incubating for 60 hours, the virus was purified with iodixanol gradients and further purification through a mustang Q membrane. Titers of recombinant AAV were determined by real-time PCR.

EXAMPLE 2

Treating Genetic Eye Disease by Means of Gene Therapy

Two methods of administering viral vectors into the eye were tested in order to test the delivery of gene therapy agents in vivo. The modes of administration were by injecting the viral vectors via subretinally (FIG. A-D) and intra-vitreally (FIG. E-I).

The virus used in this study was AAV2/2. As a control, Wild type AAV2/2.CMV. eGFP was used, and the test agent was PMAAV-GST. CMV. eGFP. The virus was injected into five week old C57BL/6 female mice. The mice were sub-retinal injected with virus (2.26×109 vg/eye). Three weeks later, the mice were anesthetized and the pupils were dilated. They were placed on a stereotactic platform, and dynamic fluorescent fundus photographs were taken. Four weeks later, the mice were sacrificed and the eyes were enucleated and fixated in 4% of paraformaldehyde. The tissue sections were cut and mounted. The expression of eGFP was observed under fluorescent microscope.

Three weeks after subretinal injection of wild type AAV2/2.CMV.eGFP and PMAAV-GST.CMV.eGFP, fluorescent imaging in live animals showed relative infection efficiencies. The targeting peptides used in this experiment was GSTPPPM (SEQ ID NO: 1). Speckled regions of GFP positivity were observed in AAV2/2 injection eyes, whereas there were broad and uniform GFP signals in PMAAV-GST eyes (FIG. 2). In other experiments, the targeting peptide was GETRAPL (SEQ ID NO: 4).

Four weeks after subretinal injection, PMAAV-GST.CMV.eGFP targeted the retinal pigment epithelium (RPE) and Outer Nuclear Layer (ONL) layers, and some cells in the ganglion cell layer (GCL). AAV2/2 targeted the outer plexiform layer (OPL) primarily (FIG. 3).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A modified adeno-associated virus (AAV) capsid protein comprising an ocular cell targeting peptide, wherein the targeting peptide comprises a sequence up to 10 amino acids in length that comprises GSTPPPM (SEQ ID NO: 1), in an amino to carboxy orientation or in a carboxy to amino orientation, and wherein the targeting peptide targets an AAV to an ocular cell.

2. The capsid protein of claim 1, wherein the targeting peptide is 8 or 9 amino acids in length.

3. The capsid protein of claim 1, wherein the targeting peptide is inserted between the capsid residues at AAV2 capsid positions P34-A35, T138-A139, A139-P140, G453-T454, N587-R588, and/or R588-Q589 of SEQ ID NO:8.

4. The capsid protein of claim 1, wherein the targeting peptide is inserted after the capsid residues at AAV9 capsid positions D384, G385, I560, T561, N562, E563, E564, E565, N704, and/or Y705 of SEQ ID NO:11.

5. The capsid protein of claim 1, wherein the capsid protein comprises or consists of SEQ ID NO:9.

6. The capsid protein of claim 1, wherein the targeting peptide targets a diseased ocular cell.

7. The capsid protein of claim 6, wherein the targeting peptide targets an ocular cell in a subject that has retinitis pigmentosa, maculopathies, Leber's congenital amaurosis, early onset severe retinal dystrophy, achromatopsia, retinoschisis, ocular albinism, oculocutaneous albinism, glaucoma, Stargardt disease, choroideremia, age-related macular degeneration, Spinocerebellar Ataxia type 7 (SCAT), color blindness, or lysosomal storage diseases that affect the cornea.

8. The capsid protein of claim 1, wherein the AAV capsid is AAV1, AAV2, AAV3, AAV4, AAV5, AAV6, AAV7, AAV8, AAV9, AAV10, AAVRh74 (Rhesus macaque-derived AAV), AAVRh10, or modified capsids of these serotypes.

9. A nucleic acid sequence encoding the modified capsid as described in claim 1.

10. The nucleic acid sequence of claim 9, comprising the nucleic acid sequence GGGTCGACGCCGCCTCCTATG (SEQ ID NO:2).

11. A viral vector particle comprising the capsid protein of claim 1.

12. The viral vector particle of claim 11, wherein the viral vector particle further comprises a nucleic acid sequence encoding a nucleic acid of interest.

13. The viral vector particle of claim 12, wherein the nucleic acid of interest is a therapeutic agent.

14. The viral vector particle of claim 13, wherein the therapeutic agent is an enzyme or an RNAi molecule.

15. The viral vector particle of claim 13, wherein the therapeutic agent is Ataxin 7 miRNA, Retinal pigment epithelium-specific 65 kDa protein (RPE 65), vascular endothelial growth factor (VEGF) inhibitor, soluble VEGF receptor 1 (sFLT1) (Rab escort protein-1) REP1, L-opsin, rhodopsin (Rho), phosphodiesterase 6B (PDE6B), ATP-binding cassette sub-family A member 4 (ABCA4), lecithin retinol acyltransferase (LRAT), Retinal degeneration slow/Peripherin (RDS/Peripherin), Tyrosine-protein kinase Mer (MERTK), Inosine-5 prime-monophosphate dehydrogenase type I (IMPDHI), guanylate cyclase 2D (GUCY2D), aryl-hydrocarbon interacting protein-like 1 (AIPL 1), retinitis pigmentosa GTPase regulator interacting protein 1 (RPGRIP1), guanine nucleotide binding protein alpha transducing activity polypeptide 2 (GNAT2), cyclic nucleotide gated channel beta 3 (CNGB3), retinoschisin 1 (Rs1), ocular albinism type 1 (OA1), oculocutaneous albinism type 1 (OCA1) tyrosinase, P21 WAF-1/Cipl, platelet-derived growth factor (PDGF), Endostatin, Angiostatin, arylsulfatase B, or beta-glucuronidase.

16. A pharmaceutical composition comprising the viral vector particle of claim 11 and a pharmaceutically acceptable carrier.

17. An isolated host cell transduced by or comprising the viral vector particle of claim 11.

18. A method of treating an ocular disease in a mammal comprising administering the viral vector of claim 11 to the mammal.

19. A method to deliver an agent to the eye of a subject, comprising transducing ocular cells with the viral vector of claim 11 so that the transduced ocular cells express the therapeutic agent and deliver the agent to the eye of the subject.

20. The method of claim 19, wherein the transduced ocular cells are within or comprise retina outer plexiform layer (OPL).

21. The capsid protein of claim 6, wherein the targeting peptide targets an ocular cell in a subject that has Mucopolysaccharidosis (MPS) IV and MPS VII.

* * * * *

UNITED STATES PATENT AND TRADEMARK OFFICE
CERTIFICATE OF CORRECTION

PATENT NO. : 10,472,650 B2  
APPLICATION NO. : 15/551869  
DATED : November 12, 2019  
INVENTOR(S) : Beverly L. Davidson et al.

It is certified that error appears in the above-identified patent and that said Letters Patent is hereby corrected as shown below:

On the Title Page

Item (73), Assignee, please delete "University of Iowa Research Foundation, Iowa City, IA (US)" and insert -- University of Iowa Research Foundation, Iowa City, IA (US); Fondazione Telethon, Rome (IT) -- therefor.

Signed and Sealed this  
Thirty-first Day of December, 2019

Andrei Iancu  
*Director of the United States Patent and Trademark Office*